United States Patent
Rose et al.

(10) Patent No.: US 11,160,419 B2
(45) Date of Patent: Nov. 2, 2021

(54) GRINDERS, ANALYZERS, AND RELATED TECHNOLOGIES

(71) Applicant: Sorry Robots LLC, New York, NY (US)

(72) Inventors: Samantha Rose, New York, NY (US); Scott Heimendinger, Seattle, WA (US); Tasche Streib, Boise, ID (US); John Laz, Boise, ID (US); Michael Egan, Chicago, IL (US); Christian Lester, Long Beach, CA (US); Brian Rose, New York, NY (US)

(73) Assignee: Sorry Robots LLC, Novato, CA (US)

( * ) Notice: Subject to any disclaimer, the term of this patent is extended or adjusted under 35 U.S.C. 154(b) by 594 days.

(21) Appl. No.: 15/492,975

(22) Filed: Apr. 20, 2017

(65) Prior Publication Data

US 2018/0055288 A1 Mar. 1, 2018

Related U.S. Application Data

(60) Provisional application No. 62/325,324, filed on Apr. 20, 2016.

(51) Int. Cl.
*A47J 42/44* (2006.01)
*A47J 42/56* (2006.01)
(Continued)

(52) U.S. Cl.
CPC ............... *A47J 42/44* (2013.01); *A47J 42/38* (2013.01); *A47J 42/40* (2013.01); *A47J 42/56* (2013.01);
(Continued)

(58) Field of Classification Search
CPC .. A47J 42/44; A47J 42/38; A47J 42/40; A47J 42/56; G01N 33/0001; G01N 33/0063; G01N 33/14; G01N 23/0254
See application file for complete search history.

(56) References Cited

U.S. PATENT DOCUMENTS

| | | | |
|---|---|---|---|
| 4,496,817 A | 1/1985 | Smith | |
| 6,783,089 B2 | 8/2004 | Lassota | |

(Continued)

FOREIGN PATENT DOCUMENTS

| | | |
|---|---|---|
| CA | 2490179 A1 | 12/2003 |
| CN | 1476805 A | 2/2004 |

(Continued)

OTHER PUBLICATIONS

Examination Report No. 1 for Australian Application No. 2017254698; dated Mar. 20, 2019; 4 pages.

(Continued)

*Primary Examiner* — Brian W Jennison
(74) *Attorney, Agent, or Firm* — Perkins Coie LLP

(57) ABSTRACT

Grinders, analyzers, and related technologies are described herein. The grinders can hold foodstuff that is periodically ground. The analyzers can analyze the foodstuff to determine information about the state of the foodstuff. Algorithms can be used to determine how to process the foodstuff, how to use the foodstuff, and/or when to discard the foodstuff. The grinder can be a portable, rechargeable electric coffee grinder configured to monitor the freshness of the coffee beans. When coffee beans become stale, they can be discarded and the coffee grinder can be refilled with fresh coffee beans.

15 Claims, 13 Drawing Sheets

(51) Int. Cl.
    *A47J 42/40*     (2006.01)
    *A47J 42/38*     (2006.01)
    *G01N 33/00*     (2006.01)
    *G01N 33/14*     (2006.01)
    *G05B 23/02*     (2006.01)

(52) U.S. Cl.
    CPC ..... *G01N 33/0001* (2013.01); *G01N 33/0063* (2013.01); *G01N 33/14* (2013.01); *G05B 23/0254* (2013.01)

(56) References Cited

U.S. PATENT DOCUMENTS

| | | | | |
|---|---|---|---|---|
| 2003/0025012 | A1* | 2/2003 | Lassota | A47J 31/42 241/34 |
| 2006/0191319 | A1* | 8/2006 | Kurup | G01N 33/02 73/23.34 |
| 2008/0175963 | A1* | 7/2008 | Pope | A47J 31/44 426/231 |
| 2014/0242239 | A1* | 8/2014 | Boggavarapu | A47J 31/3633 426/433 |
| 2015/0136496 | A1 | 5/2015 | Rego | |
| 2016/0063833 | A1* | 3/2016 | Schultz | G08B 19/00 340/522 |

FOREIGN PATENT DOCUMENTS

| | | |
|---|---|---|
| CN | 101309622 A | 11/2008 |
| CN | 103932596 B | 1/2017 |
| JP | H11-108871 A | 4/1999 |
| JP | H11108871 A | 4/1999 |
| JP | 2001104161 A | 4/2001 |
| JP | 3972757 B2 | 6/2007 |
| WO | 2012127412 A1 | 9/2012 |
| WO | 2016075147 A1 | 5/2016 |

OTHER PUBLICATIONS

International Search Report and Written Opinion for counterpart International Application No. PCT/US2017/028678; dated Jul. 25, 2017; 18 pages.
Extended European Search Report for European Application No. 17786651.4; dated Feb. 3, 2020; 7 pages.
Office Action in Chinese Application No. 201780025076.1; dated Aug. 6, 2020; 17 pages.

* cited by examiner

GRINDERS, ANALYZERS, AND RELATED TECHNOLOGIES

CROSS-REFERENCE TO RELATED APPLICATION

This application claims priority to and the benefit of U.S. Provisional Patent Application No. 62/325,324, filed Apr. 20, 2016, entitled "GRINDERS, ANALYZERS, AND CONNECTED SERVICES," which is incorporated herein by reference in its entirety.

TECHNICAL FIELD

The present disclosure relates to grinders, analyzers, and related technologies. In particular, several embodiments are directed to grinders, substance analyzers, and connected devices and services.

BACKGROUND

Over the past 10 to 20 years, consumers have developed sophisticated preferences for coffee drinks. Although many factors contribute to producing an excellent cup of coffee, one significant factor is the freshness of the coffee beans themselves. When coffee beans are roasted, they undergo a myriad of chemical transformations to produce the complex flavors and aromas that are extracted to produce coffee drinks. Over time, however, those flavors and aromas fade. Unfortunately, it is difficult to determine the freshness of beans in order to maximize the quality of coffee grounds for producing desired coffee drinks.

SUMMARY

At least some embodiments are foodstuff sensing apparatuses. Although the passage of time is often closely correlated with a decline in freshness, many other factors can contribute as well. The factors can include, for example, storage temperature, oxygen or air exposure, characteristics of the foodstuff, and process of the foodstuff. The factors can be analyzed to determine information for reporting to a user. The user can use the information to determine, for example, whether and how to use the foodstuff. The sensing apparatus can be part of a grinder, a storage container, food processing equipment, cooking apparatus, or the like.

In some embodiments, a portable, rechargeable electric coffee grinder has an integral storage container. The storage container can hold coffee grounds that are analyzed by a sensing apparatus. The factors of coffee bean staling can include, for example, storage temperature, oxygen exposure, whether the beans are kept whole or pre-ground, characteristics of the beans, and the roasting process. The factors can be analyzed to determine information for reporting to a user. The user can use the information to determine, for example, whether and how to use the coffee beans. In other embodiments, the portable, rechargeable electric grinder is configured to grind other items, such as spices (e.g., peppers), seeds, dried vegetables/fruit, or the like.

The grinder can be connectable to a base with the sensing apparatus. The sensing apparatus can include one or more charging devices (e.g., devices for wirelessly charging the coffee grinder), an analyzer, and other components for evaluating operation of the grinder, coffee beans/grounds, foodstuff, or the like. In some embodiments for coffee beans, the sensing apparatus can include one or more sensors configured to detect one or more compounds released by the beans to evaluate, for example, flavor characteristics, aromatic characteristics, bean freshness, roast characteristics, and/or other coffee bean/ground information. For example, a sensor can detect (VOCs) released by the coffee beans, grounds, foodstuff, or other items. A processor can analyze signals from the sensor to monitor changes in the beans to determine grind settings for producing grounds (e.g., high-quality grounds). The sensing apparatus can monitor degradation of the coffee beans that will lead to undesired flavors and reduced aroma. Operation of the electric coffee grinder can be automatically controlled based on, for example, user-specific flavor characteristics, aromatic characteristics, grind characteristics, and/or threshold freshness. In other embodiments, the sensing apparatus is integrated into the coffee grinder.

In some embodiments, a grinding system includes a grinder and a sensing base. The grinder can include a chamber and a grinding element. The chamber can hold coffee beans that are ready to be ground. The grinding element can be configured to grind the beans to produce coffee grounds suitable for producing a coffee drink. The sensing base is coupleable to the grinder to establish fluid communication with the chamber. In one embodiment, the grinder can be set on a platform of the sensing base to establish such fluid communication. The sensing base can be configured to analyze one or more gases from the chamber. For example, air from the chamber can be drawn into the sensing base, which can evaluate compounds in the air, concentration of gases in the air, or other information indicative of the state of the beans. The coffee beans can be evaluated with or without obtaining temperature information.

The grinding element can be configured to deliver coffee grounds directly into a removable container. The removable container can be removed to access fresh grounds. In some embodiments, the grinding element is positioned directly above the removable container when the coffee grinder is supported on a horizontal surface. This allows grounds to fall directly into the container. The direct drop interface ensures that substantially all of the grounds are removed from the grinder when the container is removed. This avoids, limits, or substantially prevents grounds from accumulating within the grinder while minimizing heat buildup to maintain flavor profiles. Accumulated grounds could later mix with fresh grounds, thereby producing a mixture of stale and fresh grounds. Accordingly, the direct drop interface can consistently produce fresh grounds.

The sensing base can be configured to charge an internal power supply of the grinder. Charging can be performed via a wireless or wired connection. In one embodiment, the grinder is charged inductively. In another embodiment, a contact or connector (e.g., a plug) of the sensing base electronically contacts a contact or connector of the grinder. The user can remove the grinder from the sensing base to grind coffee at any location. The grinder or a storage container can weigh less than about 10 lbs, 7.5 lbs, or 5 lbs for convenient transport and can be reinstalled on the sensing base when desired to recharge the internal power supply.

The sensing base can include one or more compound sensors, temperature sensors, mass sensors, or the like. The compound sensors can be VOC sensors or other sensors capable of analyzing gases. In other embodiments, the sensors can be incorporated into the grinder, such that the grinder can analyze the coffee beans independent of whether it is coupled to the sensing base. In one embodiment, the grinder and sensing base are both capable of analyzing the coffee beans. When the grinder is separated from the sensing base, the grinder can analyze coffee beans or grounds. When the grinder is coupled to the sensing base, the sensing base can analyze coffee beans or grounds, perform calibration routines, program the grinder, or the like. The grinding system can also be configured to hold other foodstuff, including spices, seeds, dried vegetables/fruit, fresh vegetables/fruit, liquids (e.g., fruit juice), or the like.

In another embodiment, a system comprises a sensor and a controller. The controller is configured to receive data from the sensor and is programmed to determine information about foodstuff held in the system. The information can include, without limitation, freshness information, forecasted freshness information, consumption rates, temperature information, user inputs (e.g., user preferences), combinations thereof, or the like. In certain embodiments, the system is a container for holding foodstuff, a coffee bean grinding system, a portable coffee grinder, a lid for a container, or another suitable container. Additional sensors can be coupled to the controller.

In yet another embodiment, a computer implemented method for analyzing foodstuff comprises determining information about the foodstuff. Freshness information can be determined for food based on gases associated with the food. In one embodiment, gases from a holding chamber containing coffee beans, or other foodstuff, can be analyzed to evaluate freshness of the coffee beans. The gases can include emissions from the coffee beans. In one embodiment, a computing device can automatically provide information to a user by transmitting the information via a network. The computing device can be part of a coffee grinder capable of sending information to the user's computer, smart phone, tablet, wearable device (e.g., smart watch) or another computing device. In some embodiments, the computing device can include a computer, controller, or another device capable of receiving and analyzing signals from sensors.

In further embodiments, a system can include one or more analyzers each configured to analyze a characteristic of foodstuff. One analyzer can include sensors that detect VOCs released by foodstuff. In one embodiment, the analyzer can monitor changes in the food and can provide such information to users. The system can be a coffee bean grinder, an espresso machine, a coffee maker, a food storage container, food processing equipment, a cooking device (e.g., a crock pot, an oven, etc.), or the like. The analyzers can include VOC sensors, gas sensors (e.g., oxygen sensors, nitrogen sensors, etc.), light sensors (e.g., UV sensors), temperature sensors, optical sensors, or the like. The system can further include an input device, such as a dial, push button, keypad, touch screen, switch, or another device suitable for accepting user input. A user can control the analyzers via the input device. The system can also include an output device, such as a display screen, an indicator, an audio device, or another device suitable for providing user feedback. A display screen can display bean or grind information, recommended grind settings, status information, alerts, and other information. An indicator can be used to notify a user of an event.

In further embodiments, a grinder can be a portable, rechargeable electric coffee grinder configured to monitor the freshness of the coffee beans. When coffee beans become stale, they can be discarded and the coffee grinder can be refilled with fresh coffee beans. Algorithms can be used to determine how to process the foodstuff, how to use the foodstuff, and/or when to discard the foodstuff. The foodstuff can be spices, seeds, fruit, cinnamon sticks, vegetables, or the like.

In some embodiments, a coffee grinder includes a holding chamber configured to hold coffee beans, a grinding element operable to grind the coffee beans, and emission sensors. Each emission sensor can be configured to detect emissions from the coffee beans held in the holding chamber. The coffee grinder can further include a controller communicatively coupled to the emission sensors and programmed to determine information about the coffee beans based on output from the emission sensors. In one embodiment, the coffee grinder can include a main housing containing the holding chamber and grinding element. A sensing base can be detachably coupled to the main housing so as to establish fluid communication with the holding chamber. The sensing base can include the emission sensors. Additionally, the sensing base can recharge the coffee grinder.

In certain embodiments, a grinding system includes a grinder including a chamber and a grinding element and a sensing base coupleable to the grinder to establish fluid communication with the chamber. The sensing base is configured to analyze gases from the chamber to evaluate coffee beans in the chamber. The grinding system can be configured to hold and grind different types of items, such as coffee beans, pepper, or the like.

In some embodiments, the coffee bean grinding system includes a sensor and a controller. The controller is communicatively coupled to the sensor and is programmed to determine information about coffee beans held in the coffee bean grinding system based, at least in part, on output from the sensor. The information can include coffee bean freshness information, forecasted coffee bean freshness information, and/or environmental information. The environmental information can include humidity information, exposure to light information, and/or temperature information (e.g., bean temperature, hopper temperature, etc.).

A method for analyzing coffee beans includes receiving bean-specific data related to characteristics of the coffee beans. The bean-specific data can include a temperature correction factor, a bean quantity correction factor, a bean correction factor, a roast date correction factor, and/or bean age factor. Emissions information (e.g., concentrations of emissions in air exposed to the beans) related to emissions from the beans is received. Information about the beans is determined based on the bean-specific data and the emissions information.

In another embodiment, a method includes receiving signals from a sensor of a coffee grinder and identifying a signal that satisfies a predetermined condition. An event associated with the satisfied predetermined condition is then determined. At least one action can be performed based on the event.

In further embodiments, a system includes a holding chamber configured to hold foodstuff, means for grinding the foodstuff, means for detecting one or more emissions from the foodstuff held in the holding chamber, and means for determining information about the foodstuff based on output from the at least one emission sensor. The means for detecting one or more emissions can include one or more emission sensors, environmental sensors, or the like. The means for grinding the foodstuff can include a grinding element. The means for determining the information can include one or more controllers, processors, and/or computing device. The means for detecting can include one or more sensors configured to detect one or more compounds released by the foodstuff to evaluate, for example, flavor characteristics, aromatic characteristics, freshness, and/or other foodstuff information. For example, a sensor can detect (VOCs) released by the foodstuff, such as coffee beans, grounds, spices, or other items. In one embodiment, the means for grinding can be eliminated. For example, the system can be a sealable storage container or coffee machine.

DETAILED DESCRIPTION

Figure 1:
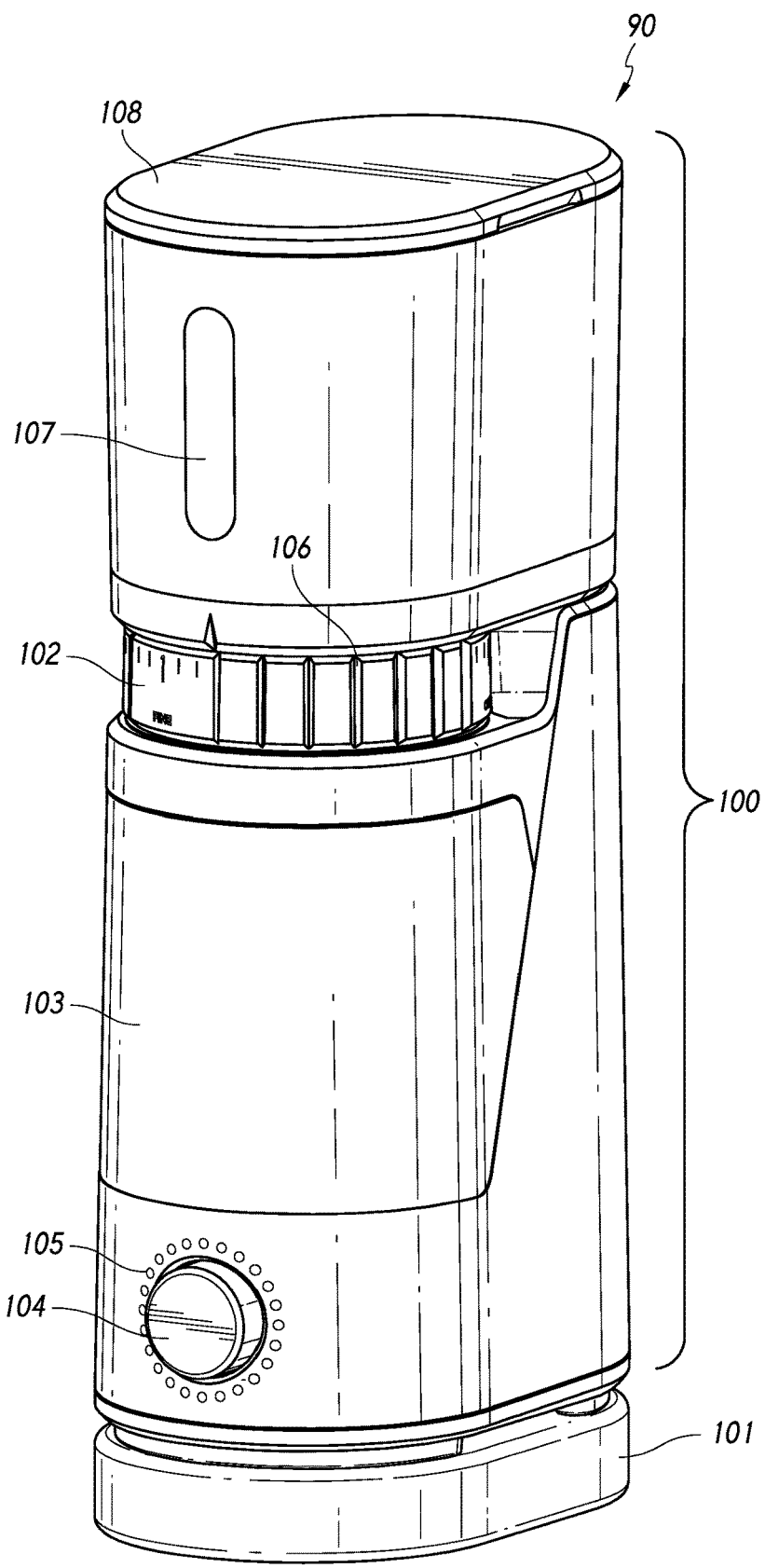
FIG. 1 is an isometric view of a coffee bean grinder system in accordance with an embodiment of the technology.

FIG. 1 is an isometric view of a grinding system 90 in accordance with an embodiment of the technology. The grinding system 90 can include a portable grinder 100 ("grinder 100") and a sensing base 101. The grinder 100 can store intact coffee beans and can grind the coffee beans. As coffee beans age, they emit emissions of various substances into the surrounding air to which they are exposed. These emissions can include VOCs or other detectable substances. The grinding system 90 can analyze the air exposed to the coffee beans to determine information about those beans without damaging or otherwise altering the beans. A hopper holding the beans can be isolated from the surrounding environment to ensure that coffee bean emissions can be accurately detected and analyzed. The sensing base 101 can collect values that are used in a freshness algorithm for generating freshness information for the beans.

The grinder 100 can include a dosing timer knob 104 and a grind adjustment element 102. The dosing timer knob 104 can be rotated to set a grinding time. Indicators 105 (one identified) can be dosing timer indicator elements positioned about the dosing timer knob 104. The grind adjustment element 102 can be used to adjust grinding settings. To start the grinding process, the user can push the dosing timer knob 104 to activate a grinding mechanism. When a set time on the timer has expired, the grinder 100 stops the grinding mechanism to complete the grinding cycle. A cup 103 can be removed from the grinder 100 to access the fresh grounds.

A display 107 can indicate when to discard unused beans, when to replenish beans, and/or how to operate the grinding system 90. The displayed information can include, without limitation, freshness information, bean usage history, grind settings, and/or information (e.g., brewing instructions, drink recipes, etc.) for using the grounds. For example, the displayed information about the beans can include, but is not limited to, UV exposure, moisture content, acidity characteristics, or other information. A user can use the grind adjustment element 102 to select the grind settings based on the displayed information. In other embodiments, the grinding system 90 can automatically adjust grind settings based upon the collected values.

The sensing base 101 can contain one or more sensors that measure the chemical concentrations of substances, such as volatile compounds, in the air exposed to the coffee beans and can include a set of components that enable the analysis of sensor readings and/or network communication. In single sensor embodiments, the sensing base 101 includes a single VOC gas sensor that responds to molecules belonging to the aldehyde family of compounds, as well as toluene. In multi-sensor embodiments, the sensing base 101 can include sensors configured to detect relevant gases, such as carbon dioxide, ethanol, benzene, ketones, or other gases identified as indicators of bean deterioration, such as 2-butanone, 2-methylfuran, and similar compounds. The readings of the sensors can be sampled continually or periodically (e.g., between once per second and once per minute) and are used as inputs into the freshness algorithm, a roast algorithm, a brew algorithm, or the like. The grinder 100 can be aligned with and placed on sensing base 101 to establish both electrical and fluid communication internal components of the sensing base 101. The sensing base 101 can analyze the coffee beans and recharge an internal power supply of the grinder 100. The grinder 100 can rest of the sensing base 101 for any desire period of time. The charged grinder 100 can be lifted off of the sensing base 101 to grind coffee beans at any desired location.

Figure 2:
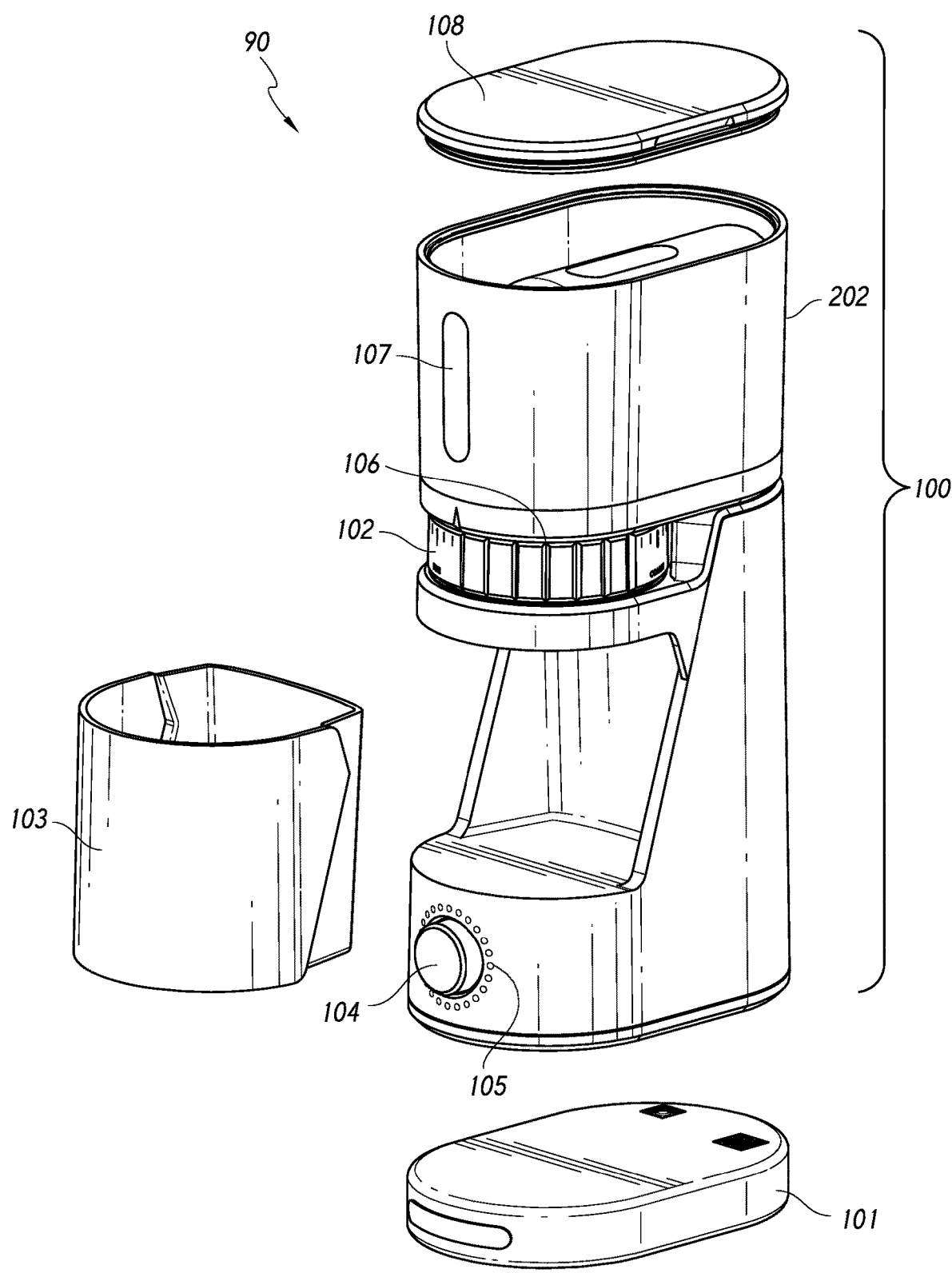
FIG. 2 is an exploded isometric view of the coffee bean grinder system of FIG. 1.

FIG. 2 is an exploded isometric view of the grinding system 90. The grinder 100 can include a removable lid 108 and a hopper 202. The removable lid 108 can be removed to access the inside of the hopper 202. The cup 103 can be a catch cup, grounds container, bin, or another suitable container for storing and carrying grounds. In other embodiments, grounds can fall directly into a portafilter. The portafilter can extract the grounds under pressure in an espresso machine. Temperature changes can affect the compounds released by the beans and thereby affect the bean monitoring. Accordingly, thermally isolating the portafilter or heat-generating components can increase the accuracy of analyses performed on the beans. The thermal isolation can also prolong the freshness of the stored beans because heat can accelerate the staling process, as well as minimizing or limiting thermal effects to temperature-sensitive sensors.

The display 107 can be a semi-transparent or transparent window for viewing the contents of the bean hopper 202 to allow a user to visually inspect the level of beans. In some embodiments, the display window 107 can include a screen (e.g., a digital screen) capable of displaying information, including one or more of the following statuses: bean quantity, bean freshness, grind fineness setting, battery charge or charging state, error conditions, maintenance notifications, or device status information.

Figure 3:
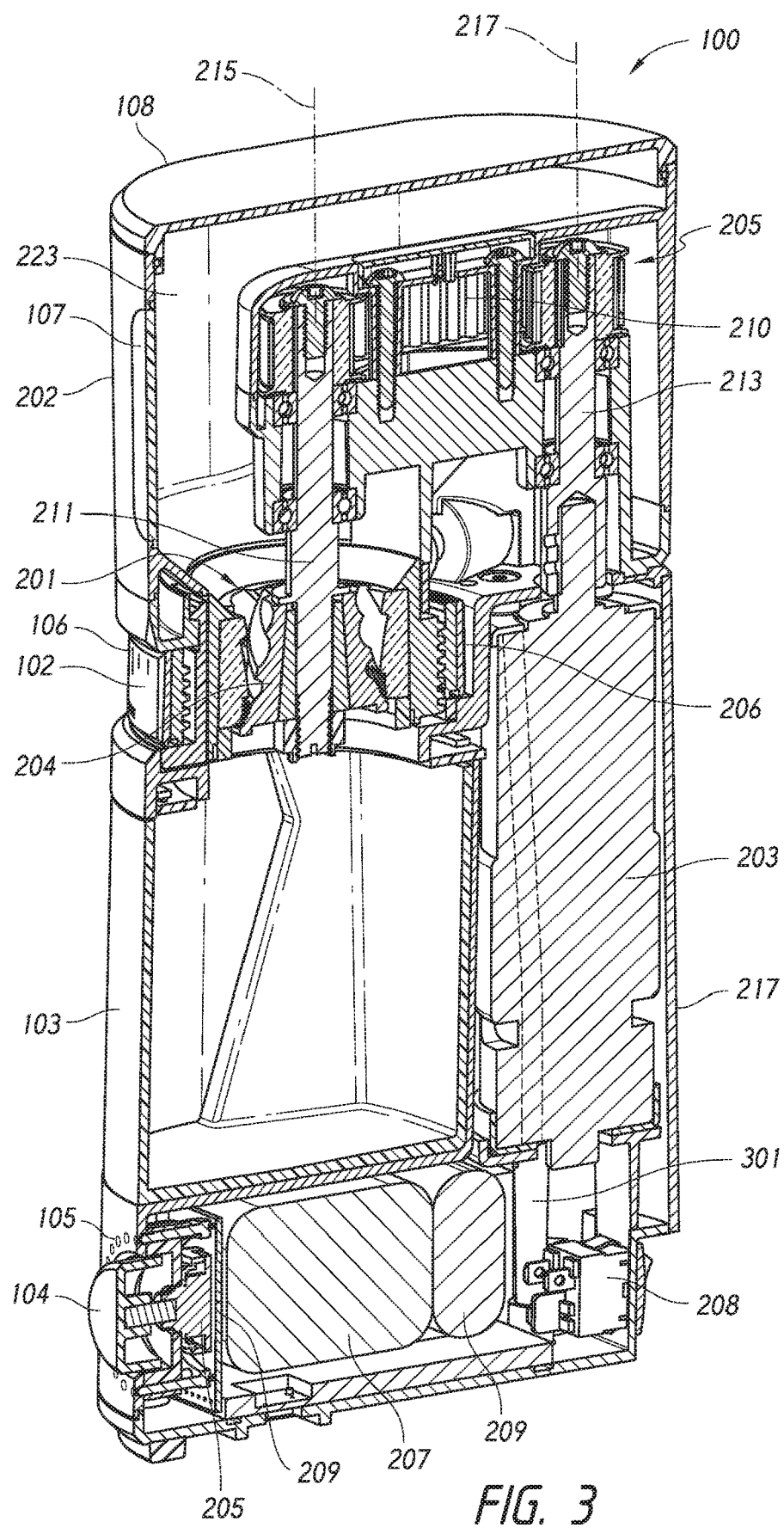
FIG. 3 is a cross-sectional view of a coffee bean grinder in accordance with an embodiment of the technology.

FIG. 3 is a cross-sectional view of the grinder 100 in accordance with an embodiment of the technology. The hopper 202 is generally positioned above the grinding mechanism or element 201 ("grinding element 201") and can be straight walled or tapered. The grinding element 201 can include two complementary cones in a "conical burr grinder" configuration. The cones can have features that cooperate to smash, crush, and/or grind coffee beans. For example, each of the cones can have ridges, grooves, or additional features for interacting with beans. The distance between these cones is determined by the grind adjustment element 102. The grinding element 201 can provide non-discrete settings for precise control of the grind setting. By gradually changing the distance between the cones, precise grind control can be achieved. As very minute changes to the grind fineness may have a measurable impact on the extraction or brewing of the coffee, the stepless grind adjustment may be advantageous. In other embodiments, the grinding element 201 can be configured for providing discrete settings and can include a stepper motor, stops, or other features for moving the cones to preset configurations. This allows for repeatable grind settings. In one embodiment, the grinding element 201 can have both non-discrete and discrete modes.

The fineness adjustment wheel 102 can be rotated to select a course grind, a medium grind, or a fine grind. Course grinds are suitable for use with a French press, a percolator, etc. Medium grinds are suitable to produce drip coffee. Fine grinds (including super fine grinds) are suitable for use with espresso machines and for producing Turkish coffee. The display window 107 can display the grind setting, recommend coffee recipes, recommend brew settings, or other information. In manual embodiments, a user can manually rotate the grind fineness adjustment wheel 102 while viewing the fineness setting detected by the detector 206. In automated embodiments, the grinder 100 may include a device that moves the adjustment wheel 102. The device can include, without limitation, a motor, a servo, an actuator, or another device suitable for controllably moving the adjustment wheel 102. In some embodiments, the grind fineness adjustment wheel 102 can include markings 106 in the form of printed or embossed features capable of serving as reference points for specific grind fineness.

A grind fineness setting detector 206 ("detector 206") can monitor the grind setting and can be a digital encoder, an optical encoder, a variable potentiometer, an electromechanical detector, or the like. The setting of the grind fineness adjustment wheel 102 is used to enhance the accuracy of the dosing functionality—the finer the grind setting, the longer it will take to grind an equal mass of beans. The grind time can be selected based on the grind setting to produce the desired amount of grounds. A long grind time can be selected for a fine grind setting whereas a short grind time can be selected for a coarse grind setting. The grinder 100 can automatically select an appropriate grind time based on a desired amount of grinds. A user can manually set the grind settings using the grind fineness adjustment wheel 102, and the detector 206 can determine the grind setting based on the position of the adjustment wheel 101. The detector 206 can then communicate the setting to a controller, which determines an appropriate grind time based on the setting. Although the grinder 100 may be operated independently of the sensing base 101 for the purpose of storing and grinding coffee beans, the grinding system has enhanced capabilities when the grinder 100 and sensing base 101 are used in conjunction. The sensing base 101 can collect values from sensors and can feed the values through a "freshness algorithm," along with other information provided by the user, to determine and display information about the beans' freshness, provide recommendations for the best coffee experience, and so forth.

A driver 208 can be mechanically coupled to the grinding element 201 via, for example, a connection assembly 203. The driver 208 can be a drive motor, an electric motor, a stepper motor, or another drive device powered by an internal power supply 207. The connection assembly 203 can include a motor shaft 213, a grinder shaft 211, and a drive belt 210 coupled to the motor shaft 213 and grinder shaft 211. The motor shaft 213 can be directly or indirectly coupled to an output shaft of the driver 208. The grinder shaft 211 can be connected to an inner grind element 204 (e.g., a ridged cone) of the grinding element 201. The drive belt 210 can translate the driver's 208 action to the grinder shaft 211 to operate the grinding element 201. This allows the driver 208 to be spaced apart from the hopper 202 and grinding element 201 so that generated heat by the driver 208 is thermally insulated from the stored beans. One or more insulators can be positioned to limit or inhibit heat transfer between the driver 208 and the hopper 202, thereby further limiting thermal effects to the beans. The grinder shaft 211 can be generally parallel to the motor shaft 213. For example, a longitude axis 215 of the grinder shaft 211 can be generally parallel to an axis 217 of the motor shaft 213. The belt 210 can extend in a direction generally transverse to one or both axis 215, 217. The shafts 211, 217 can be at other positions to provide for different configurations.

The driver 208 may be directly coupled to the grinding element 201. For example, a driver can be located in the hopper 202, and a shaft of the driver can be directly coupled to a rotatable cone of the grinding element 201. In other embodiments, the grinding element 201 may be driven by a hand crank or other drive mechanism. The configuration of the connecting assembly 203 can be selected based on the position and location of the driver 208. In various embodiments, the connection assembly 203 can include, without limitation, one or more axles, shafts, gears, reducers, belts, chains, couplers, bearings, and/or connectors. The configuration of the connection assembly 203 can be selected based on the configuration of the grinding element 201. For example, a connection assembly 203 for driving a flat burr element can be different from one for driving a blade grinding element.

The grinding element 201 can be oriented vertically, such that gravity feeds whole beans in from the above hopper 202 and causes the ground beans to fall into the catch cup container 103 below. An axis of rotation (e.g., axis 215) about which the grinder shaft 211 rotates can be in a generally vertical orientation (e.g., ±5 degrees, ±3 degrees, ±2 degrees from vertical). Because ground beans fall directly into the container 103, old grounds do not accumulate within the grinder 100. This direct-drop interface can prevent or reduce old rancid or sub-prime coffee grounds from combining with fresh grounds. In some embodiments, both cones of the grinding element 201 are positioned directly above the container 103 such that the exit of the grinding element 201 is directly above an opening of the container 103. The exit can be a gap between the complementary cones or another suitable exit feature. Other types of grinding elements can discharge grounds at other locations.

The internal power supply 207 can be positioned within a housing 217 and can be in electrical communication with the driver 208. The internal power supply 207 can be a rechargeable battery capable of providing sufficient power to operate the driver 208. In some embodiments, the driver 208 includes an electric motor and, in one embodiment, is powered by a set of batteries 207 (e.g., disposable Alkaline batteries or rechargeable Alkaline, Ni2N, NiCD, NiMH, or Lithium ion batteries) that enable the grinder to function, even when disconnected from a continuous power supply. In rechargeable embodiments, the batteries 207 can be charged by a power supply and a power conditioning circuit. In an alternate embodiment, the grinder 100 may not contain batteries and may be powered by a power supply directly.

As the action of brewing coffee depends not only on grind fineness but also on the quantity of the grounds, it is often advantageous for the grinder 100 to produce a repeatable, consistent amount of ground coffee. This is accomplished by the dosing timer 205. The user sets a grinding time—in typical usage between 5 seconds and 60 seconds—that corresponds to the desired volume of beans to grind. The user enters this setting by turning the dosing timer knob 104. The setting is registered and displayed to the user on the dosing timer indicator lights 105. The user may then start the dosing process by pushing or pulling the dosing timer knob 104. The dosing timer can activate the motor 208 via communication through a controller 209. When the set time on the timer has expired, the controller 209 stops the motor 208 and the grinding is complete.

The dosing functionality can also be accomplished by sensing the quantity of the beans, rather than by setting a timer. In such an embodiment, a feedback loop can exist between the controller 209 and a sensor that detects the quantity of grinds. The sensor may, in some embodiments, measure the mass of the grinds as they accumulate in the catch cup 103. In other embodiments, the sensor may sense the volumetric quantity of the grounds by using a contactless distance sensor, such as an infrared or ultrasonic rangefinder, or by using a resistive or conductive contact-based sensor, to measure the height of the beans in the hopper 202. The number and types of sensors can be selected based on the desired monitoring. Contact based sensors can be positioned along the wall of the hopper 202 or the lid 108. Sensors for measuring the mass of accumulated grinds in the catch cup can be located along a surface of the grinder that supports the catch cup.

The grinder 100 may contain components for drawing gases away from the hopper 202 and toward the sensor(s) in the sensing base 101 (not shown in FIG. 3). To measure chemical components in the gas headspace surrounding the beans in the hopper 202, headspace gases can be removed from the hopper chamber 223 via a headspace connection conduit 301. The headspace connection conduit 301 may be a single tube (a portion of the tube is illustrated in phantom line). In other embodiments, the headspace connection conduit 301 can be two tubes connected to a pump to circulate the gases of the hopper headspace down toward the sensing base 101 and back again along a closed loop. Other types of fluid connections can be used to provide fluid communication between the hopper 202 and the sensing base 101. Valves, such as one-way valves, can be used to ensure one-directional flow from the headspace to the sensors. Pumps, including vacuum devices, can be part of the grinder 100 or the sensing base 101. The pumps can operate periodically to draw head space gases through the grinder 100 and into the sensing base. The pumps can be powered by the internal power supply 207 or another suitable power supply, such as a power supply within the sensing base or an external power supply. Additionally or alternatively, the catch cup 103 can also be in fluid communication with the sensing base directly or indirectly. In some embodiments, gases exposed to the ground beans in the catch cup are drawn by the grinder 100 and delivered into the sensing base. The fluid components and configuration of the grinding system can be selected based on the number of gases to be analyzed and the location of the substances to be analyzed.

The cover 108 can form a suitable seal (e.g., a fluid-tight seal, an air-tight seal, or the like) to limit or substantially prevent surrounding fresh air from entering into the hopper chamber 223. In other embodiments, the sensing base can compensate for air leaks associated with continuous fresh air entering the hopper 223. When the hopper 223 is opened to discard or refill the grinding system, the grinding system can recognize that fresh air has been introduced, so the headspace coffee bean emissions will be at relatively low levels for a period of time. As the emissions gradually accumulate in the headspace chamber 223, the headspace gases can be analyzed to accurately determine characteristics of the coffee beans.

Figure 4:
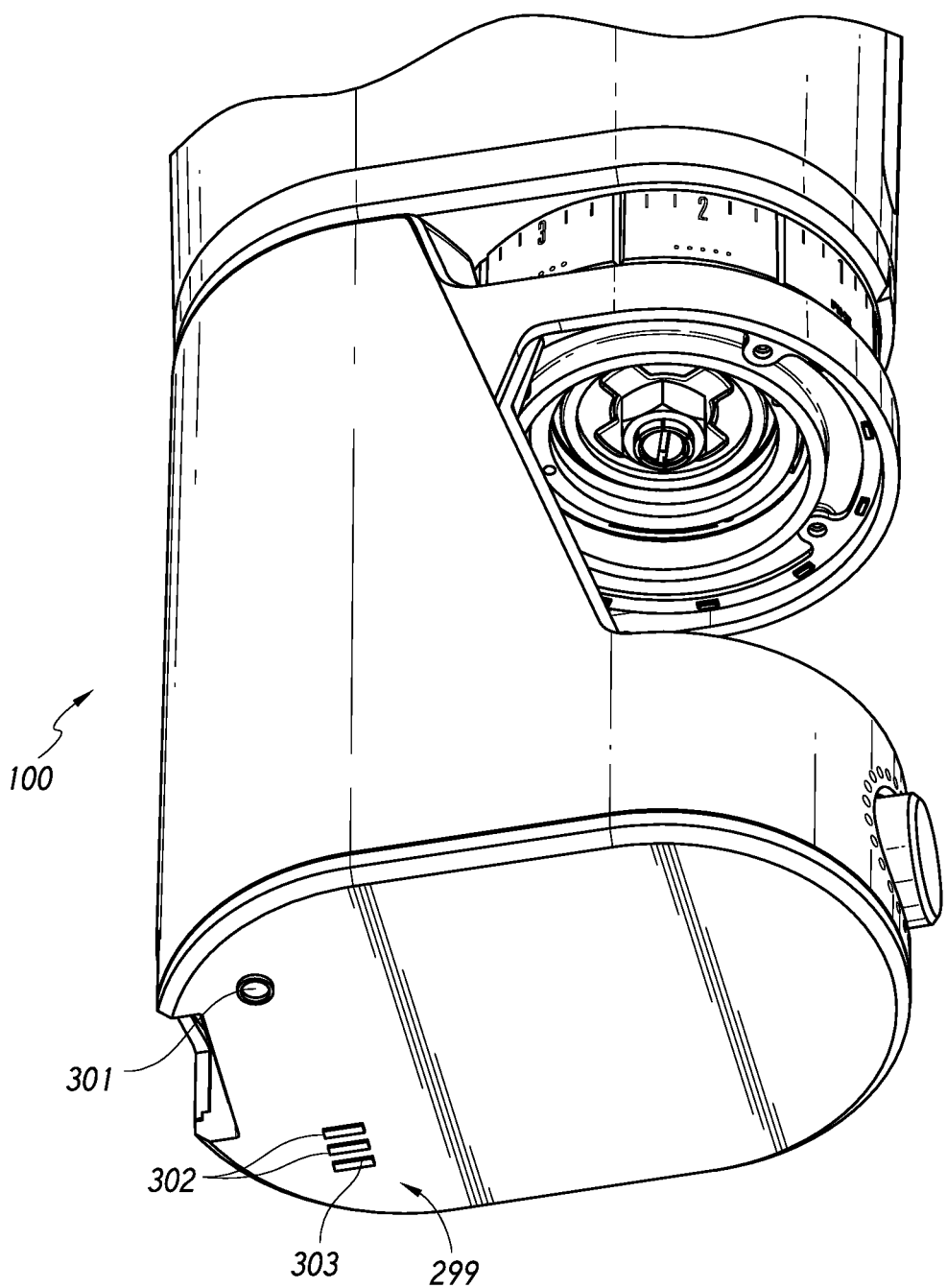
FIG. 4 is a bottom, front, and left-side view of the coffee bean grinder of FIG. 3.

FIG. 4 shows the bottom of the grinder 100 with an electronic interface in the form of electronic contacts 299 for interfacing with the sensing base. The electronic contacts 299 can include a power supply connection 302 (illustrated as two contacts) and a controller connection 303 (e.g., a microcontroller communication connection) for enabling communication and coordination between the functions of the grinder and the functions of the sensing base. In other embodiments, the power supplied to the grinder 100 may be transferred through a contactless, inductive charging mechanism. Similarly, in alternate embodiments, the controller communication across devices may be accomplished through wireless connections.

Figure 5:
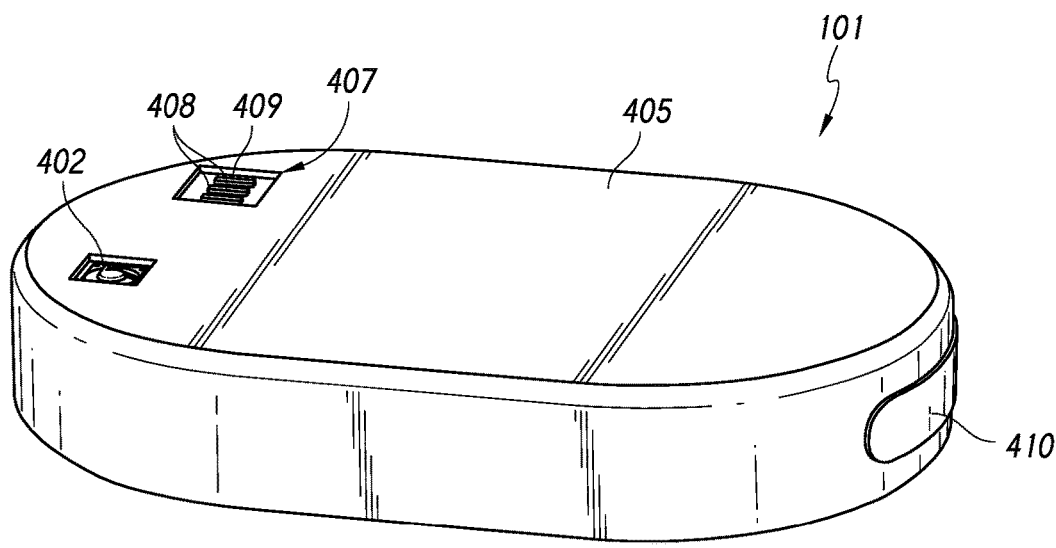
FIG. 5 is an isometric view of a sensing base in accordance with an embodiment of the technology.

FIG. 5 is an isometric view of a sensing base 101 suitable for grinding systems. The sensing base 101 can include electronic contacts 407, a display 410, and an airflow device in the form of a fan 402 ("fan 402"). The electronic contacts 407 can include a grinder power supply connection 408 (illustrated as two contacts) and a controller connection 409 for enabling communication and coordination between the functions of the grinder and the functions of the sensing base. When the grinder is positioned on the sensing base 101, the connections 408, 409 (FIG. 5) can contact the corresponding connections 302, 303 (FIG. 4). The sensing base 101 can then recharge the power supply of the grinder.

The display 410 can provide information, including, without limitation, the power state of the grinder network status (e.g., network connection, Bluetooth state, Wi-Fi connection state, etc.), bean information (e.g., freshness of the beans in the hopper, inferred mass of the beans in the hopper, etc.), error conditions or maintenance notifications, changed state of grinder, usage history, calibration information, or other status information. The display 410 and the grinder's display (e.g., display 107 of FIG. 1) can display the same or different information, and the user can program the grinding system to display desired information. For example, the display 410 can display grind system information whereas the display 107 (FIG. 1) can display coffee bean information.

Figure 6:
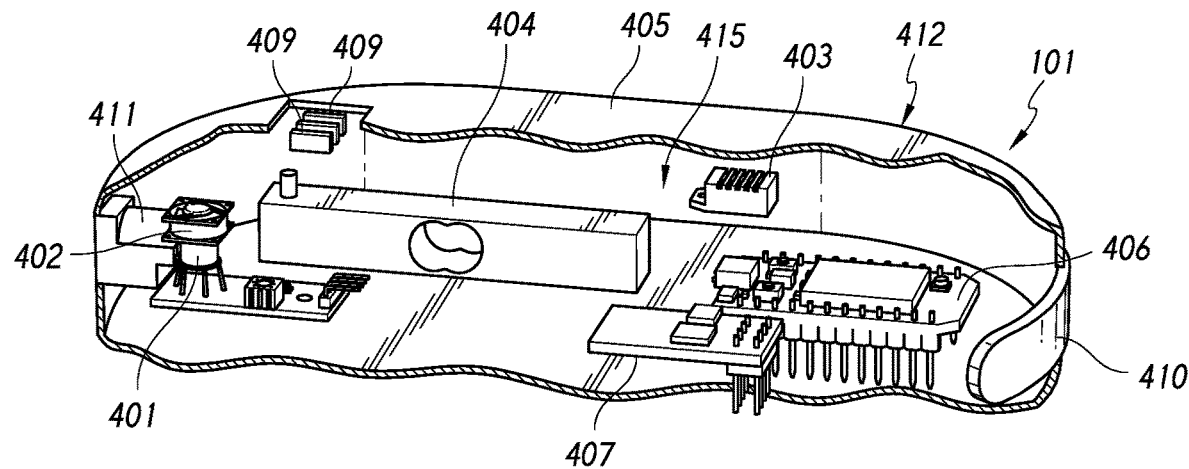
FIG. 6 is a cutaway view of the sensing base of FIG. 5.

FIG. 6 is a cutaway view of the sensing base 101. The fan 402 can be positioned to cause gas to be delivered from the grinder to a sensor 401. When the sensing base 101 is coupled to the grinder, the fan 402 can be fluid communication with the headspace chamber 223 (FIG. 3) and the sensor 401. In some embodiments, the fan 402 can be positioned generally above the sensor 401 and below a headspace connection tube 301 (FIG. 4) of the grinder 100. When the fan 402 is turned on, it can draw air from the headspace into and through the connection tube 301 and then pushes the air through the sensing base 101 and to the sensor 401. In this manner, the fan 402 can draw the air exposed to the coffee beans through the grinder and to appropriate components in the sensing base 101. In open loop embodiments, the analyzed air can be exhausted out of the sensing base 101 via vents. In closed loop embodiments, the fan 402 or another pump may be used to circulate air between the hopper and a sensing chamber that contains one or more sensors along a closed loop. The sensing chamber can be located within the sensing base 101. In yet other embodiments, the fan 402 may be absent. For example, an airflow device (e.g., a fan or blower) can be positioned within the hopper and can be operated to cause headspace air to flow to the sensing base 101. In another embodiment, there may be no forced air movement. Concentration gradients of the headspace gases can allow natural equilibration throughout a sensing or connection tube or other fluid connectors.

With continued reference to FIG. 6, the sensing base 101 can include a power input 411 that is configured to receive power from a power source, such as a household outlet. In some embodiments, the sensing base 101 can include an integral DC transformer, circuitry, and/or additional optical components. In other embodiments, a transformer is external to the sensing base 101 (e.g., "wall wart" transformer). A housing 412 of the sensing base 101 can protect a set of components or analyzer 415 configured to measure, analyze, and/or communicate (e.g., via a network) data or information. A single VOC gas sensor (e.g., sensor 401) can detect molecules belonging to the aldehyde family of compounds, as well as toluene. Additional sensors may detect relevant gases, such as carbon dioxide, ethanol, benzene, ketones, or other gases identified as indicators of bean deterioration, such as 2-butanone, 2-methylfuran, or the like. The readings of the sensors can be continuously or periodically sampled (typically between once per second and once per minute) and can be used as inputs into one or more algorithms (e.g., freshness algorithms). In some embodiments, the sensors may be replaced by an "electronic nose" sensor, which can sense and discriminate a number of VOCs, airborne chemicals, or the like.

A temperature sensor 403 can detect the ambient temperature, temperature of the sensing base 101, or the like. Data collected from the temperature sensor 403 can be used as an input into the freshness algorithm, because it can contribute to the calculation. Gas sensors are often subject to fluctuations in their readings based on temperature, the temperature readings can be used to compensate for such fluctuations. Analytical or theoretical techniques can be used to determine and compensate for temperature effects. Temperature sensors in the hopper can monitor temperatures of the headspace air to analyze the relationship between ambient temperatures and bean staling because high temperatures can accelerate bean staling. Compensation or calibration programs can be performed on freshness algorithms based upon the measured temperatures of the beans as well. The sensing base 101 and grinder may also include other environmental sensors for monitoring relative humidity, light exposure, and other environmental conditions, which would also be used as inputs into the freshness algorithm.

The sensing base 101 can include a mass sensor 404 of the analyzer 415 to measure the mass of the grinder. In one embodiment, the mass sensor 404 is a load cell that supports a platform 405 (e.g., a movable platform, a deformable platform, a floating platform, etc.) above the mass sensor 404. The platform 405 can have a generally horizontal surface for supporting the grinder 100 such that when the grinder is placed on top of the platform 405, the force of its mass is transferred to the mass sensor 404. In an alternate embodiment, the grinder 100 sits directly on top of one or more mass sensors. The sensing base 101 can detect mass of the grinder (including coffee beans therein) without the use of the platform 405.

Because the grinder has a known constant mass, any additional mass detected by the mass sensor may be calculated or inferred to be the mass of coffee, either as beans in the hopper or as grounds in the catch cup. The inferred mass of the beans can be used as an input into one or more algorithms. As the quantity of the beans in the hopper decreases, so will the concentration of volatile gases detected by the sensing base 101. The calculated mass of the beans can be used for calibration, including calibration of the absolute concentration of volatile gases, to provide a consistent freshness reading. The relationship between the mass of the beans and the concentration of volatile gases can be periodically updated to maintain desired accuracy. Updating and optimization can be performed by an internal controller of the grinding system, a remote server, a remote device, or the like. As the user grinds and removes coffee grounds, the mass (e.g., calculated or inferred mass of the beans) of the beans will decrease. This information can be sent to a network, a cloud service, or another device for determining usage information. For example, coffee bean usage (e.g., changes in mass), inferred mass, or other events can be a timestamped event used to calculate the historical and forecasted rate of consumption.

Operation of the grinding system can be based on detection of one or more events. If an event is detected, the grinding system can take appropriate action, including notifying a user of the event, logging data, timestamping data, calibrating the grinder, adjusting algorithms, and so on. In some embodiments, the grinding system can determine the occurrence of an event by detecting changes in gas concentrations, changes of the mass of whole beans, changes in temperature, or the like. The magnitude and/or rates of change may be associated with events of interest selected by the user. In some modes of operation, the grinding system can determine the occurrence of an event by comparing detected values with set threshold values. In one exemplary embodiment, a user can be notified when the temperature of the beans is at or above a maximum desired temperature (e.g., a temperature that may significantly accelerate deterioration of the beans). Once the user is notified, the user can move the grinding system to an appropriate cool place. In another mode of operation, the grinding system can notify the user when it determines that the coffee beans have deteriorated a certain amount. This way the user can discard stale or rancid coffee beans before using them.

With reference to FIG. 6, a controller 406 can be configured to be in communication with the grinder 100 and the sensors 401, 403, 404. The controller 406 can include onboard storage, memory, analog-to-digital converters, a central processing unit, and an operating system to process the functions of the sensing base 101. The controller 406 can be connected to a communication device 407 configured to communicate with the grinder 100, a remote device, and/or a network. The operation of the sensing base 101 and grinder can be coordinated via, for example, a network. The communication device 407 can be a Wi-Fi chip or a wireless networking device that is integral or separate from the controller 406. In other embodiments, the networking or communication device 407 may be a Bluetooth chip, cellular communication chip, nearfield wireless communication device, or a hardwired (e.g., Ethernet) networking interface.

Figure 7A:
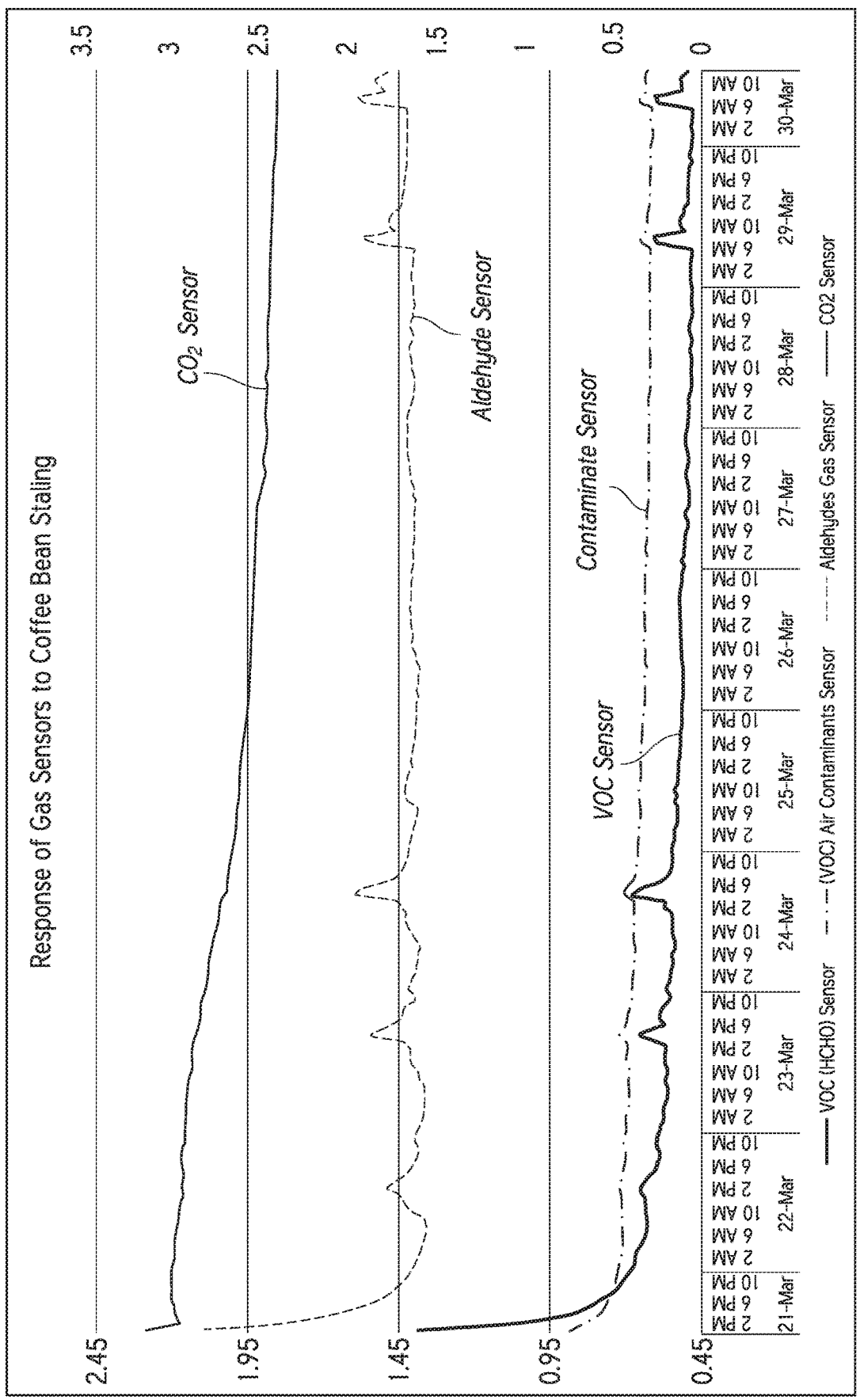
FIG. 7A is a plot of output from sensors versus time.
Figure 7B:
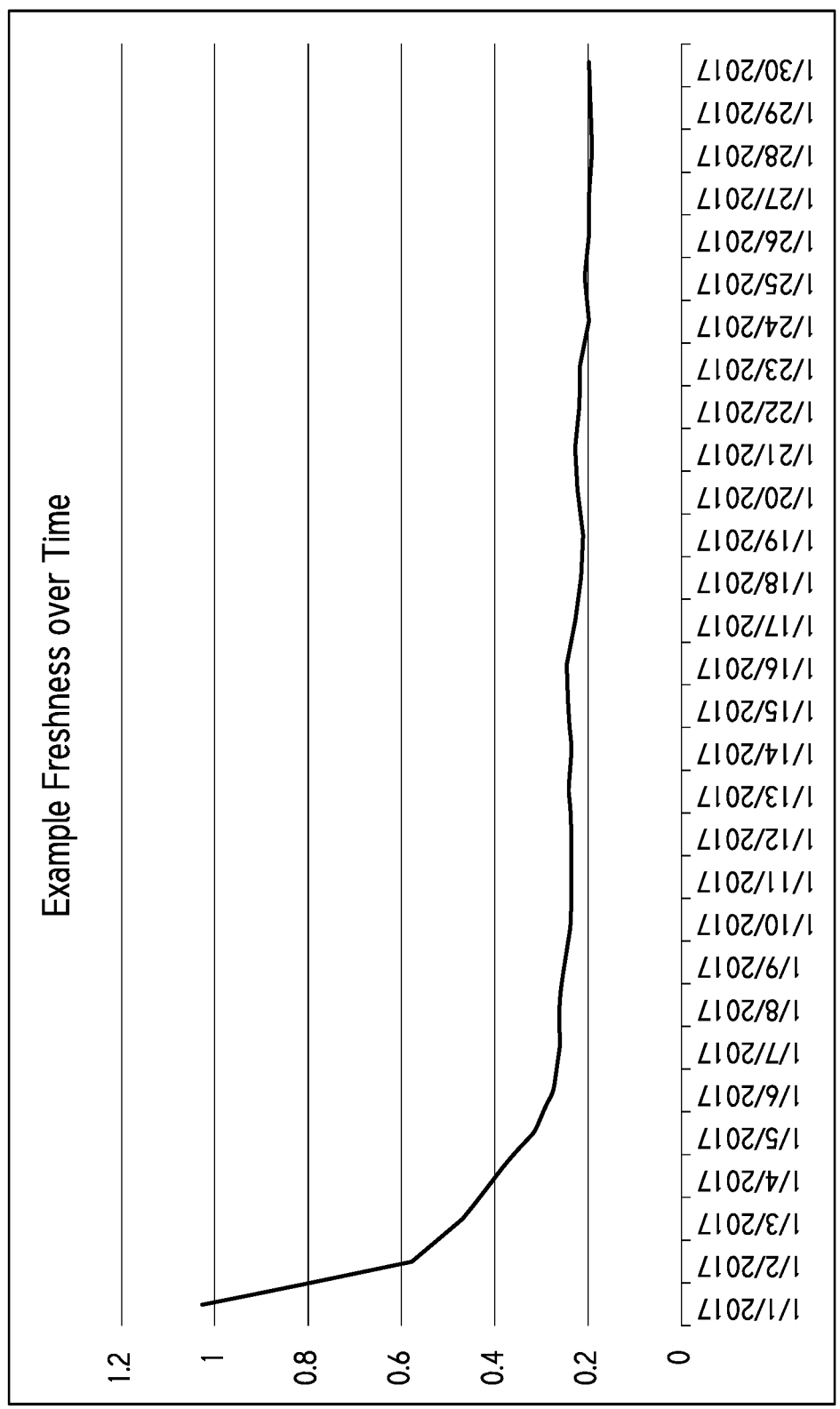
FIG. 7B is a plot of freshness values versus time based on sensor data.

FIG. 7A is a plot of output from sensors for monitoring coffee beans versus time as the coffee beans become stale. FIG. 7B is a plot of freshness values versus time based on sensor data. Referring now to FIG. 7A, volatile gas concentration in the headspace gases can be used to monitor the coffee beans because gas concentrations can be correlated, often tightly correlated, to bean freshness. Multiple compounds can be measured to determine freshness. Data was collected from four gas sensors to track volatile concentrations over a period of nine days. The concentrations of volatile gases measurably declines over time. The illustrated data is for a set amount of coffee beans. As coffee beans are removed from a hopper, the rate of emissions will decrease because the amount of coffee beans decreases. The decrease associated with usage of coffee beans can be used to determine the applicable rate of emissions for a given mass of coffee beans. The amount of emissions, rate of change in emissions, and other collected values can be used to determine information about the coffee beans.

Without being bound by theory, it is believed that the spikes (e.g., March 23rd, 4 PM) are caused by sudden changes in the temperature of the environment surrounding the analyzer. The temperature-induced emissions or increases in emission can be identified. Temperature monitoring can be performed to provide a correction factor that is applied to the direct gas sensing. For example, if the grinding systems are used near heat generating appliances (e.g., an oven), the heat generated by the oven may affect the coffee beans. The temperature of the surrounding environment, internal chamber of the grinder, or coffee beans in cells can be monitored to identify changes in the compounds that are attributable to temperature changes. Other conditions (e.g., humidity, exposure to light, etc.) can be monitored to generate additional correction factors.

FIG. 7B shows freshness values that account for temperature and roasting to enhance accuracy. Different types of beans can have different staling characteristics. Stored programs, lookup tables, and other data used to analyze output from the sensors based, at least in part, on the staling characteristics of the beans. For example, different freshness algorithms or values for freshness algorithms can be used to monitor light-roast coffee beans and dark-roast coffee beans. The calculated freshness values of FIG. 7B are discussed further in connection with Table 1.

Figure 8:
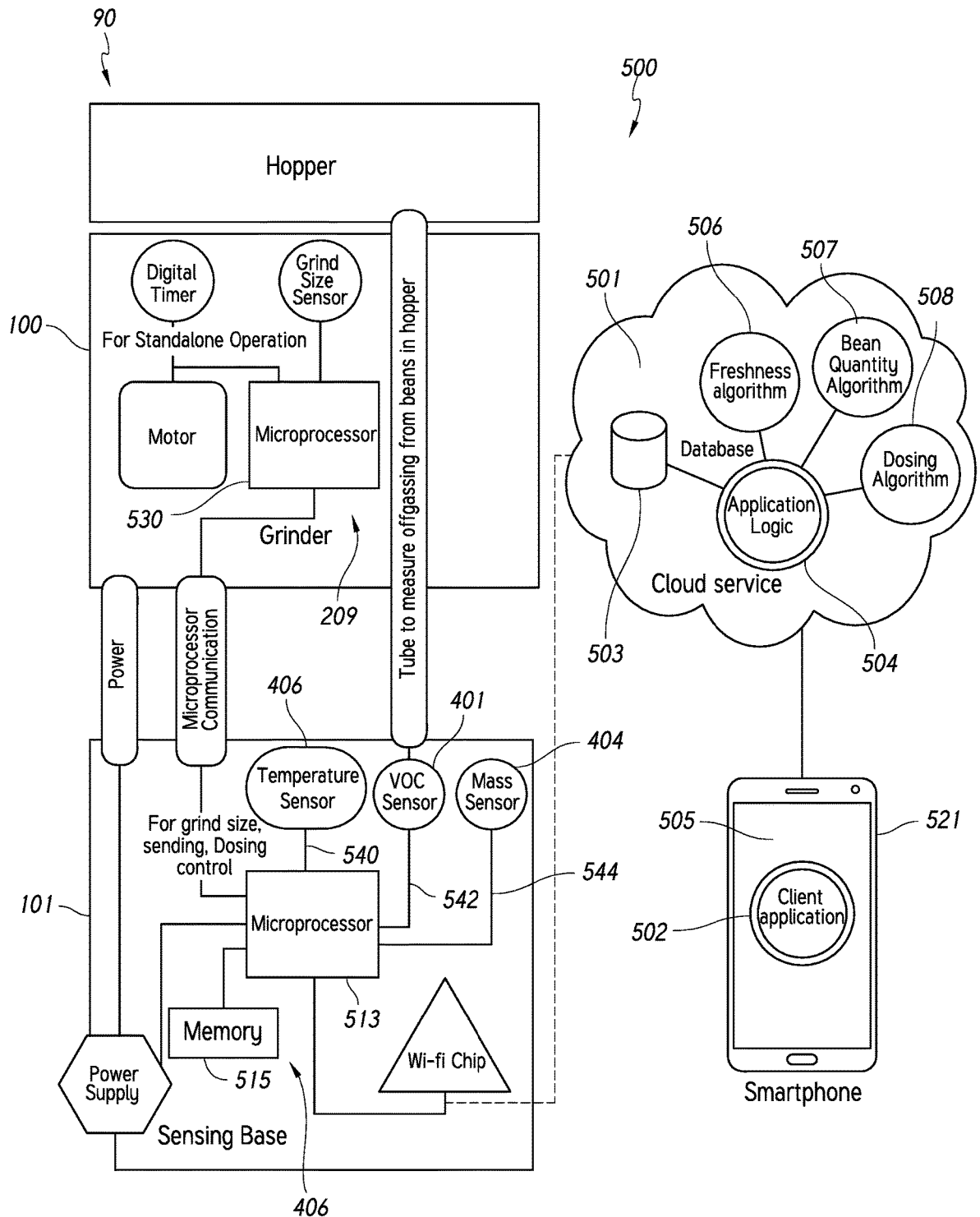
FIG. 8 is a diagram illustrating an environment in which a grinding system may operate.

FIG. 8 is a diagram illustrating an environment in which a grinding system may operate. Data can be collected from sensors of grinders and/or sensing bases to provide information about coffee beans, guidance on usage to maximize the quality of the coffee experience, or the like. This can be accomplished through the use of a remotely running computer program, remote server, and database, referred to as the cloud service 501. The user can interact with the cloud service 501 through a client application 502 via a remote device 521 (illustrated as a smartphone). The remote device 521 can also be a computer, tablet, smart watch, virtual assistant device, or the like.

The network 500 may include, without limitation, one or more servers, gateways, routers, bridges, combinations thereof, or the like. In one embodiment, the network 500 includes one or more servers and one or more websites that are accessible to users. The network 500 can send and receive information that the client computer system can utilize and can include, but is not limited to, data networks using the Transmission Control Protocol (TCP), User Datagram Protocol (UDP), Internet Protocol (IP), and other data protocols. The client computer or system can be programmed to perform the methods and techniques discussed herein.

In some embodiments, the cloud service 501 can include a database 503 and application logic 504. The database 503 can store data received from the grinding system. This information can be sent to the cloud service 501 on regular, periodic intervals (e.g., once per second, once per minute, one per day, etc.). The duration of the interval may be user-defined, or may be variable depending on environmental factors. For example, when fresh beans are added to the hopper or are ground and removed from the hopper, the grinding system may increase the frequency of readings to quickly calculate an updated freshness value. Alternately, if the grinder 100 and sensing base 101 have been idle, the grinding system 90 may reduce the frequency of readings to conserve bandwidth and storage. In some embodiments, when the grinder 100 is removed from the sensing base 101, the sensing base 101 may stop sending readings until the grinder has been reinstalled.

Each data submission from the sensing base 101 may include, among other information, the following data:
  Current values from the gas sensor(s)
  Current values from the temperature sensor or other environmental sensors (e.g., humidity)
  Current values from the load cell from which the system may calculate the inferred mass of the coffee beans
  Current value of the grind fineness setting
  Current value of the dosing timer (e.g., 25 seconds)
  An event flag. For example:
    Grinding started, grinding completed
    Dosing timer value changed
    Change in load cell reading (change in bean mass)
    Grinder removed, grinder reinstalled
    Resume from power disruption
    A unique identifier for the sensing base (e.g., GUID or serial number)
    A unique identifier for the grinder (e.g., GUID or serial number)
    The timestamp at which the readings were sampled The event flags can be selected by a user. In addition to periodic data submissions, the sensing base 101 may also send and receive messages in communication with the cloud service 501 for registration, deregistration, authentication, firmware updates, and/or other boilerplate messages following, for example, protocols and well-known patterns of Internet-of-things devices.

The user, through interacting with the client application 502, may also send and receive messages in communication with the cloud service for event notification (i.e., detection of an event), registration, deregistration, authentication, software updates, and other boilerplate messages following the well-known patterns of client applications. In one embodiment, the client application 502 displays information vie a display screen 505. The remote device 521 can be a smartphone, tablet, portable internet-connected device, computer, or another computing device. The user may find and install the client application 502 according to well-known conventions, like an "app store" marketplace.

The client application 502 allows the user to perform functions in communication with the cloud service that, in turn, communicates with the sensing base 101. These functions may include:
  Getting the current values from each of the sensors in the sensing base and grinder
  Setting the value of the dosing timer
  In some embodiments, initiating grinding, or stopping grinding
  Reading the value of the grind fineness setting, and in some embodiments, setting the value of the grind fineness setting Boilerplate functions, including registration, authorization, assigning permissions to a Wi-Fi network, updating onboard firmware, etc.

Providing the user's geographic and demographic information

The client application 502 can provide specific bean information for the beans that are loaded into the hopper or information about the user's general bean preferences or other user input. By having more specific information about the beans, the freshness algorithm can refine its calculation to produce more accurate results.

The client application 502 can provide an interface whereby the user may specify details of the beans loaded into the hopper. In one embodiment, the client application 502 prompts the user to take a photo of the UPC (barcode) on the bag of beans. The application then compares that UPC to a database of known UPCs to determine if details about the coffee may be populated from the information in the database. These details may include:

The roast type or item name

The name [brand] of the coffee

The bean species (e.g., *Arabica, Robusta*)

The marked net weight of the bag of beans

The average physical size of the bean

The application may then request the user to specify time-based information to further refine the freshness algorithm calculation. This information may include the roast date, which is typically printed on the bag, and the date of purchase.

In some embodiments, the user may manually input this information into the client application or application logic 504. In other embodiments, the grinder 100, sensing base 101, or user's client application device may automatically detect an identifier for the coffee electronically from an RFID tag, barcode, QR code, or other means of encoding data on either the coffee itself or on the container in which the coffee arrived.

A freshness algorithm 506 can combine the data produced by the sensors in the sensing base 101 and grinder 100, details about the coffee beans, and a library of known freshness information about specific coffees and coffee types to produce a freshness value that indicates the quality the user should expect to experience from the coffee. The algorithm can also use the same inputs to forecast how the quality is expected to change over time. An embodiment of the freshness algorithm is given below.

$$F = \frac{S \times \lambda_T \times \lambda_Q \times \lambda_B \times \lambda_R \times \lambda_A}{\text{Ideal } Freshness_{specificbean}} \quad \text{(Equation 1)}$$

F=Freshness value
S=Consolidated freshness sensor readings
$\lambda_T$=Temperature correction factor
$\lambda_Q$=Bean quantity correction factor
$\lambda_B$=Specific bean correction factor
$\lambda_R$=Roast date correction factor
$\lambda_A$=Bean age in the hopper correction factor The freshness value may also be calculated across a time series to produce a curve of freshness over time. The freshness value may also be forecast into the future using mathematical forecasting models. In some embodiments, the forecasting function may be a logarithmic equation derived from the historical freshness readings and adjusted by the known variables of the current temperature and existing information about the freshness decay curves of the specific bean. The correction factors can be provided by roasters or another source. In some embodiments, the grinding system 90 determines the correction factors empirically.

Table 1 below has representative coffee bean data for equation 1 that can be inputted into the freshness algorithm 506. FIG. 7B is a plot of the calculated freshness versus time based on the data.

TABLE 1

| Time | S | $\lambda_T$ | $\lambda_Q$ | $\lambda_B$ | $\lambda_R$ | $\lambda_A$ | F |
|---|---|---|---|---|---|---|---|
| Jan. 1, 2017 | 98 | 1.020 | 58 | 0.88 | 8 | 1 | 1.020392 |
| Jan. 2, 2017 | 96 | 0.960 | 71 | 0.88 | 8 | 0.5 | 0.575816 |
| Jan. 3, 2017 | 93 | 1.020 | 84 | 0.88 | 8 | 0.333333 | 0.46747 |
| Jan. 4, 2017 | 89 | 1.050 | 97 | 0.88 | 8 | 0.25 | 0.398845 |
| Jan. 5, 2017 | 85 | 0.960 | 110 | 0.88 | 8 | 0.2 | 0.315955 |
| Jan. 6, 2017 | 80 | 0.950 | 123 | 0.88 | 8 | 0.166667 | 0.274208 |
| Jan. 7, 2017 | 80 | 0.950 | 136 | 0.88 | 8 | 0.142857 | 0.259877 |
| Jan. 8, 2017 | 79 | 1.010 | 149 | 0.88 | 8 | 0.125 | 0.261552 |
| Jan. 9, 2017 | 78 | 1.010 | 162 | 0.88 | 8 | 0.111111 | 0.249575 |
| Jan. 10, 2017 | 78 | 0.990 | 175 | 0.88 | 8 | 0.1 | 0.237838 |
| Jan. 11, 2017 | 78 | 1.010 | 188 | 0.88 | 8 | 0.090909 | 0.23697 |
| Jan. 12, 2017 | 68 | 0.990 | 240 | 0.88 | 8 | 0.083333 | 0.236966 |
| Jan. 13, 2017 | 69 | 1.020 | 253 | 0.88 | 8 | 0.076923 | 0.241068 |
| Jan. 14, 2017 | 69 | 1.020 | 266 | 0.88 | 8 | 0.071429 | 0.235351 |
| Jan. 15, 2017 | 74 | 1.000 | 279 | 0.88 | 8 | 0.066667 | 0.242246 |
| Jan. 16, 2017 | 73 | 1.050 | 292 | 0.88 | 8 | 0.0625 | 0.2462 |
| Jan. 17, 2017 | 72 | 1.000 | 305 | 0.88 | 8 | 0.058824 | 0.227351 |
| Jan. 18, 2017 | 72 | 0.960 | 318 | 0.88 | 8 | 0.055556 | 0.214917 |
| Jan. 19, 2017 | 71 | 0.970 | 331 | 0.88 | 8 | 0.052632 | 0.211163 |
| Jan. 20, 2017 | 68 | 1.040 | 357 | 0.88 | 8 | 0.05 | 0.222174 |
| Jan. 21, 2017 | 70 | 1.050 | 370 | 0.88 | 8 | 0.047619 | 0.22792 |
| Jan. 22, 2017 | 74 | 0.960 | 383 | 0.88 | 8 | 0.045455 | 0.217667 |
| Jan. 23, 2017 | 70 | 1.020 | 396 | 0.88 | 8 | 0.043478 | 0.216361 |
| Jan. 24, 2017 | 70 | 0.950 | 409 | 0.88 | 8 | 0.041667 | 0.199456 |
| Jan. 25, 2017 | 70 | 0.990 | 422 | 0.88 | 8 | 0.04 | 0.205882 |
| Jan. 26, 2017 | 69 | 0.950 | 447 | 0.88 | 8 | 0.038462 | 0.198344 |
| Jan. 27, 2017 | 63 | 1.050 | 460 | 0.88 | 8 | 0.037037 | 0.198352 |
| Jan. 28, 2017 | 68 | 0.950 | 473 | 0.88 | 8 | 0.035714 | 0.192065 |
| Jan. 29, 2017 | 68 | 0.970 | 486 | 0.88 | 8 | 0.034483 | 0.19455 |
| Jan. 30, 2017 | 68 | 1.000 | 499 | 0.88 | 8 | 0.033333 | 0.199068 |

The data is for a one month period of time. The ideal freshness is 40000 and can be set by the user, a roaster, or another source. For example, a recommended ideal freshness for the coffee beans can be provided by an RFID tag, barcode, QR code, or other means of encoding data on either the coffee itself or on the container in which the coffee arrived. Referring to FIG. 8, the remote device 521 can be used to scan the barcode and then sends the information to the grinding system 90. In other embodiments, the grinder system 90 includes a RFID reader, barcode reader, or another device for obtaining information from the grinding system 90. In one exemplary embodiment, consolidated freshness sensor readings (S) can be in a range of about 68 to about 98. The temperature correction factor ($\lambda_T$) can be for normal temperature fluctuations in a residential setting, such as in a kitchen. The bean quantity correction factor ($\lambda_Q$) can be over time whereas the specific bean correction factor ($\lambda_B$) and roast date correction factor ($\lambda_R$) can be constants. The threshold freshness corresponding to stale coffee beans can be stored. For example, a user may set the desired minimum freshness to 0.3 or another suitable value.

The freshness algorithm (Equation 1) can be used with a wide range of foodstuff. For example, $\lambda_Q$ can be foodstuff quantity correction factor, $\lambda_B$ can be foodstuff correction factor, $\lambda_R$ can be foodstuff processing date correction factor, and $\lambda_A$ can be foodstuff age correction factor. One or more of the variables can be eliminated. For example, $\lambda_R$ can be eliminated for fresh fruits or vegetables, whereas $\lambda_R$ can be used for toasted foodstuff, such as spices. The Ideal Freshness can vary for different types of food.

Using the freshness algorithm, the system may provide alerts to the user. Embodiments of these alerts may include:
Freshness has fallen below a threshold value
In d days, the freshness is forecasted to fall below a threshold value
The current temperature measured by the sensing base 101 is above a threshold value
The events that trigger alerts can be selected by the user.

Under conditions in which the system does not have access to the full set of correction factor information, an approximated freshness value can be calculated, inputted by a user, or provide from another source (e.g., a remote server). This value may be less accurate than the value given by the full calculation, but it can be useful in embodiments of the system or in user behavior, wherein the full set of data is unavailable.

$$F = \frac{S \times \alpha_T \times \alpha_Q \times \alpha_B \times \alpha_R \times \alpha_A}{\text{Ideal Freshness}_{specificbean}} \quad \text{(Equation 2)}$$

F=Freshness value
S=Consolidated freshness sensor readings
$\alpha_T$=Assumed temperature correction factor (e.g., temperature at 70° F.)
$\lambda_Q$=Bean quantity correction factor
$\alpha_B$=Assumed bean correction factor
$\alpha_R$=Assumed roast date correction factor (e.g., roasted 10 days ago)
$\alpha_A$=Assumed bean age in the hopper correction factor (e.g., beans in hopper for 4 days)
Table 2 below has representative data for equation 2.

TABLE 2

| Ideal Freshness | 40000 | | |
|---|---|---|---|
| Variable | Description | Value | Notes |
| S | Consolidated freshness sensor readings | 85 | Sensor reading |
| $\alpha_T$ | Assumed temperature correction factor (e.g., temperature at 70° F.) | 1 | Calibrated to 70 F. = correction factor of 1 |
| $\lambda_Q$ | Bean quantity correction factor | 100 | ex. bean hopper is full minus 100 g |
| $\alpha_B$ | Assumed bean correction factor | 1 | Calibrated to standard bean offgassing profile = 1 |
| $\alpha_R$ | Assumed roast date correction factor (ex. roasted 10 days ago) | 10 | Assume typical roast date of 10 days old |
| $\alpha_A$ | Assumed bean age in the hopper correction factor (ex. beans in hopper for 4 days) | 0.25 | Assume beans in the hopper for 4 days = ¼ age correction factor |

The coffee grinder can request data from a remote server. In response to the request, the remote server can determine appropriate values and can send the values to the coffee grinder. The freshness value based on the data in Table 2 is 0.53. The freshness value can calculated based on the output from sensors used to determine the consolidated freshness sensor readings. Other freshness values can be selected based on user preferences and Equation 2 can be used to determine freshness of other foodstuff.

Referring to FIG. 8, the bean quantity algorithm 507 can use data from the load cell in the sensing base, the setting of the dosing timer, the grind fineness setting, and specific bean information to calculate the current and forecasted quantity of beans available in the hopper and in the user's home storage. The current quantity of beans in the hopper can be determined by direct measurement from the load cell, minus the known mass of the grinder. This quantity is referred to as the "inferred bean quantity."

The forecasted bean quantity can be calculated by applying a regression model to the historical inferred bean quantity. The regression model may be adjusted to accommodate for fluctuations in use by day of the week, periods of non-use, the current setting of the dosing timer, and grind fineness setting, as well as external factors. At least some embodiments of the external factors may include user-supplied information about the user's schedule (e.g., at home vs. traveling, morning appointments, work schedule, etc.), the weather (e.g., cold weather or rainy days could correlate with greater coffee consumption), and/or other factors. The total quantity of available beans may be calculated as the known net weight of an identified bag of beans, minus the mass that has been removed from the hopper through grinding.

FIG. 8 shows a dosing quantity algorithm 508 that can be used to generate dosing information. In the preparation of coffee drinks, precise dosing is advantageous for creating a high-quality, consistent drink. For example, some recipes specify an exact mass ratio of coffee grounds to water, with precise steep times and temperatures. A dose of ground coffee is defined by the mass of those coffee grounds. For reasons of manufacturability, measuring the mass of the grounds produced through the grinding element may be impractical. Instead, a grinding timer is used as a proxy for mass. The relationship between grinding time and dose mass may be subject to variability by factors, such as the grind fineness and the oiliness of the beans (fresh beans are very oily but will dry out over time).

The algorithm to refine the accuracy of timed dosing is based on the measured values of the grind fineness setting, the freshness of the beans, and specific bean information. As beans are ground, the mass registered by the load cell in the sensing base 101 will not change—the beans are being transferred from the hopper to the catch cup, but the total mass of the grinding system is unaltered. When the catch cup is removed, the grounds dumped out, and the catch cup replaced, the sensing base 101 can determine a decrease in the mass measured by the load cell. This mass can be equal to the mass of beans that were ground during the last grinding. The system can store this information in a database and mathematical model to build the predictive dosing quantity algorithm 508.

To calculate the correct dosing time, the user can specify, through the client application 502 or another interface, the desired dose of ground coffee. The dosing quantity algorithm can then read from the grind fineness setting, the freshness value, and the historical mathematical model to calculate a grinding time that will produce the desired dose.

In some embodiments, the freshness algorithm, bean quantity algorithm, and dosing algorithms described above may be supplanted with one or more machine-learning algorithms. Machine-learning algorithms may incorporate not only the specific user's behavior, but also draw from the behavior of all users and devices in the system to refine and improve its calculations and predictive capabilities.

A recommendation module or engine can use data to select or generate recommendations. Using an individual customer's usage data, including the specific bean types used, frequency of use, grind setting and dosage amount (usable to infer brew type), and other data supplied by the user (such as survey responses), the system can recommend other beans, brew styles, coffee equipment, coffee shops, or other offerings that may align with the user's preferences. These recommendations may be generated through clustering or affinity algorithms.

Because the systems disclosed herein are able to calculate the quantity of remaining beans, the user's consumption habits, and a forecast of bean freshness, the systems can provide value in replenishing old beans with new ones before the user exhausts his bean supply or the beans drop below an established quality threshold. Bean replenishment may be offered through a variety of business model embodiments, including:

Automatic replenishment, shipped direct-to-consumer;
Referral to online retailers (e.g., Amazon) to order replacement beans, with an affiliate commission returned to the company;
Recurring subscription model that adjusts frequency and bean type in accordance with the user's behavior and stated preferences;
Referral to local retailers; and
Analytics and insights for coffee industry partners.

Given the amount and granularity of data collected by the system, an embodiment of the technology can allow for detailed analytics on the usage of the system. These data may be valuable to coffee industry partners, including coffee retailers, bean roasters, coffee equipment manufacturers, cafes, foodservice vendors, and others. Examples of the consumer behavior insights may include:

What are the most popular specific beans or brands?
How much coffee do users consume per unit time, and how do those usage patterns cluster?
How frequently is the grinder used in a portable scenario vs. a "docked" scenario?
What are the most popular brew methods (inferred by grind fineness and dosing quantity)?
How much money are users spending on coffee, and what is their price sensitivity?
These insights may then be segmented over user-related dimensions, including:
  Age, gender, and other demographics authorized by the user;
  Geographic location and socioeconomic data associated with geography;
  User type (e.g., daily user, infrequent user, etc.); and
  Seasonal and environmental data (e.g., holiday periods, local weather, sunrise/sunset time of day).

The data can be commuted continuously or periodically to a remote server. The data can be accessed based on user requests, operation of a coffee grinder, or the like. For example, a web portal or application on a mobile device can be used to access the data. Based on the data, a user can determine which coffee beans to buy. The technology can allow for detailed analytics on the usage of other foodstuff consumption, usage, or the like.

With continued reference to FIG. 8, the sensing base 101 can include a controller 406 configured to command the grinder 100. The controller 406 can include a processor 513 and memory 515 and can be in communication with sensors 402, 401, 404. Additional sensors can be utilized. The number, position, and configuration of the sensors can be selected based on the desired functionality. To directly analyze emissions, the VOC sensor 401 can be mounted on, incorporated into, or coupled to the hopper and in communication with the processor 513 and/or a processor 530.

The programmable processor 513 can encompass all kinds of apparatuses, devices, and machines for processing data, including, by way of example, a programmable microprocessor (illustrated), a computer, a system on a chip, or multiple ones, or combinations of the foregoing. The programmable processor can include circuitry, special purpose logic circuitry, for example, a field programmable gate array (FPGA) or an application-specific integrated circuit (ASIC). The programmable processor can also include, in addition to hardware, code that creates an execution environment for the computer program in question (e.g., code that constitutes processor firmware, a protocol stack, a database management system, an operating system, or a combination of one or more of them). Sensor readings 540, 542, 544 from sensors 403, 401, 404 can be used to generate control variables.

The memory 515 can be coupled to the processor 513 and can store data, including executable instructions, collected data about coffee beans and/or grounds, and other information. The memory 515 can store instructions for monitoring coffee beans, detecting events, commanding components, and/or communicating with a system. In some embodiments, the memory 515 contains programs discussed in connection with the cloud service 501. For example, the memory 515 can include dosing algorithms, freshness algorithms, bean quantity algorithms, and application logic and can be secure memory, standard memory, or a combination of both memory types. In various embodiments, the memory 515 can be flash memory, secure serial EEPROM, secure field programmable gate array, or secure application-specific integrated circuit and can store instructions, programs, recipes, user-specific flavor characteristics, user-specific aromas characteristics, grind characteristics, and other information. The programs can be include, without limitation, compensation programs, coffee bean analysis programs, calibration programs, or other programs for monitoring or analyzing foodstuff. Compensation programs can be used to compensate for environmental conditions to enhance accuracy of freshness determinations. For example, a compensation program can compensate for temperature of facts on operation of sensors. Coffee bean analysis programs can be used to determine freshness of the coffee beans. Calibration programs can be used to continuously or periodically calibrate components and/or operation of the coffee grinder. Computer programs can be written in any form of programming language and can be stored in a portion of a file that holds other programs or data (e.g., one or more scripts stored in a markup language document), in a single file dedicated to the program in question, or in multiple coordinated files (e.g., files that store one or more modules, subprograms, or portions of code). Recipes can be consumer-specific product recipes (e.g., recipes programmed by a user), downloaded recipes, or the like and can be communicated to another device, such as a remote viewing device via a network (e.g., local network, wide area network, etc.). Remote viewing devices (e.g., device 521 in FIG. 8) can communicate directly with the grinder 80 via Z-Wave, Wi-Fi, ZigBee, Bluetooth, peer-to-peer protocols, or other methods or technology. A network connection such as provided by an Ethernet local area network (LAN) interface, or, a wireless network interface via a WiFi LAN access point provided, for example, in accordance with the I.E.E.E. 802.11 b/g/n/ac wireless or wireless network communications standard. The grinding system 90 can communicate with an automation networking device, hub, repeater according to XIO, Z-Wave or ZigBee for wired or wireless home network automation. The systems disclosed herein can provide remote web access to operate, monitor, and control grinders.

Figure 9:
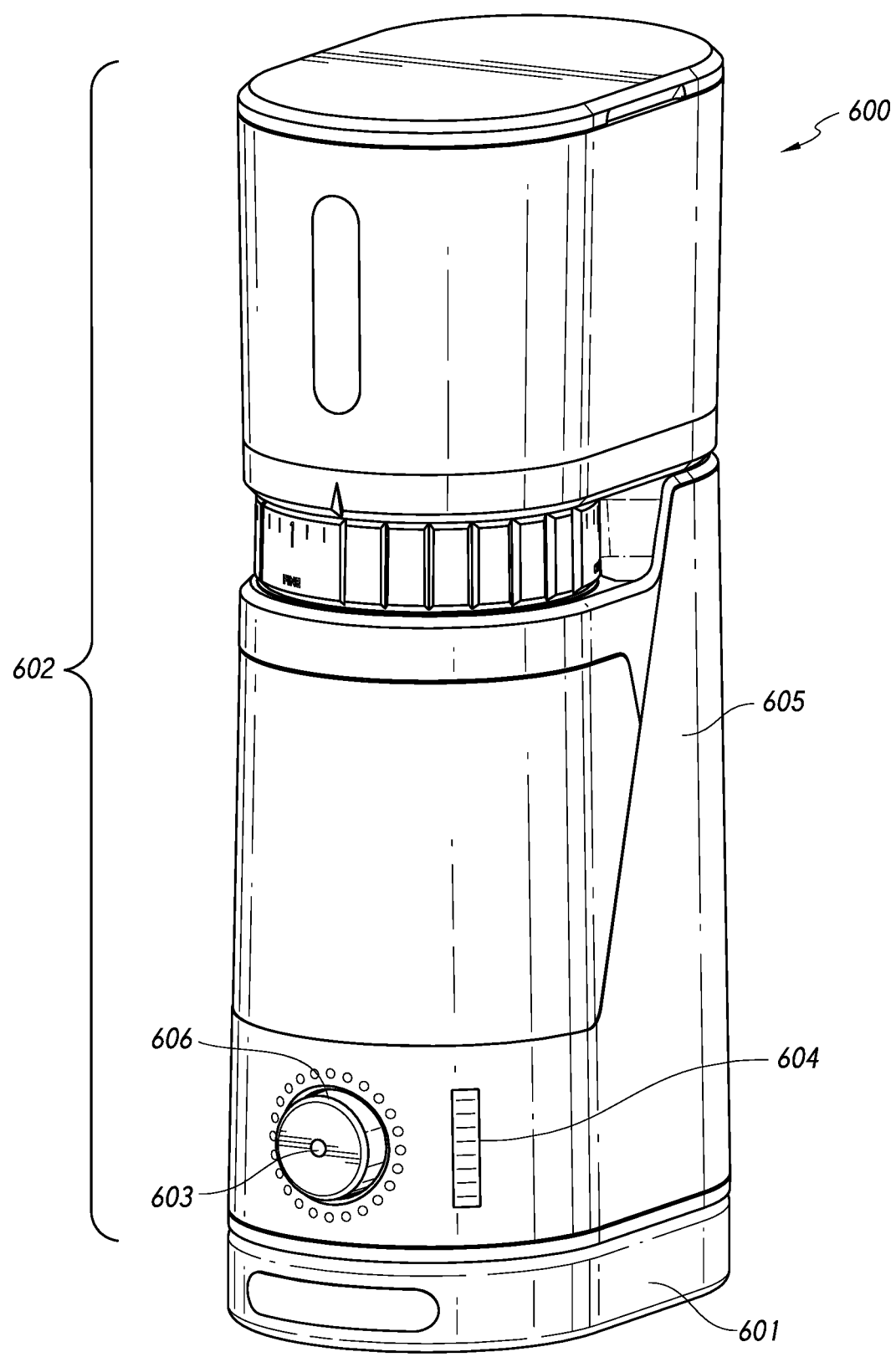
FIG. 9 is an isometric view of a grinding system in accordance with another embodiment of the technology.

FIG. 9 is an isometric view of a grinding system 600 in accordance with another embodiment of the technology. The relevant description of the grinding system 90 of FIGS. 1-6 and 8 applies to the grinding system 600. The grinding system 600 can include a coffee grinder 602 and an integrated sensing base 601. A one-piece or multi-piece housing 605 can protect internal components. This embodiment is well suited for commercial settings, like coffee shops, where the portability of the grinder components is not required.

Figure 10:
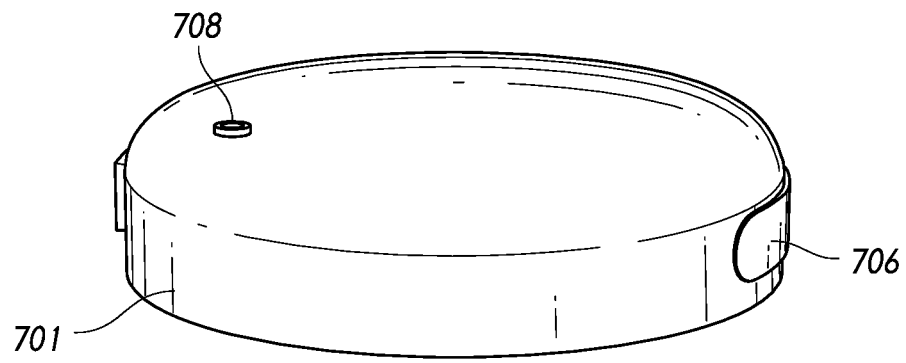
FIG. 10 is a side elevational view of an analyzer in accordance with another embodiment of the technology.
Figure 11:
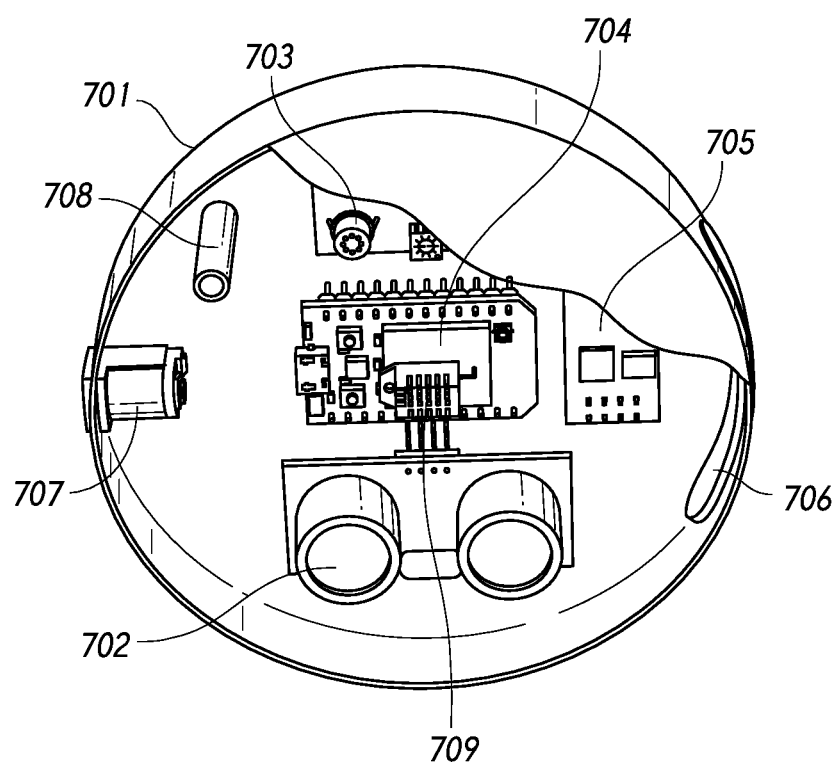
FIG. 11 is a cutaway bottom view of the analyzer of FIG. 10.

FIG. 10 is a side elevational view of a foodstuff analyzer 701 in accordance with another embodiment of the technology. FIG. 11 is a cutaway bottom view of the analyzer 701. The analyzer 701 can be in the form of a sensing lid that can be placed above any container of beans, such as the existing hopper of a commercial coffee grinder. Referring now to FIG. 11, the analyzer 701 may contain one or more sensors, including a VOC or other gas sensor 703, a temperature and humidity sensor 709, and other environmental sensors. In a lid configuration, it can sense the quantity of the beans in the hopper. As an alternative to sensing their mass from below, the sensing lid may employ a distance sensor 702, such as an ultrasonic rangefinder, infrared reflectivity distance sensor, or other means of sensing the height of the beans in a container. The sensing lid also contains a power supply 707, microcontroller 704, and network interface 705, such as a Wi-Fi chip. For the purpose of communicating status, bean freshness, or other information, the sensing lid may also contain a display 706. In some embodiments, the lid 108 of FIG. 1 can includes the components of the analyzer 701 to enhance monitoring.

Figure 12:
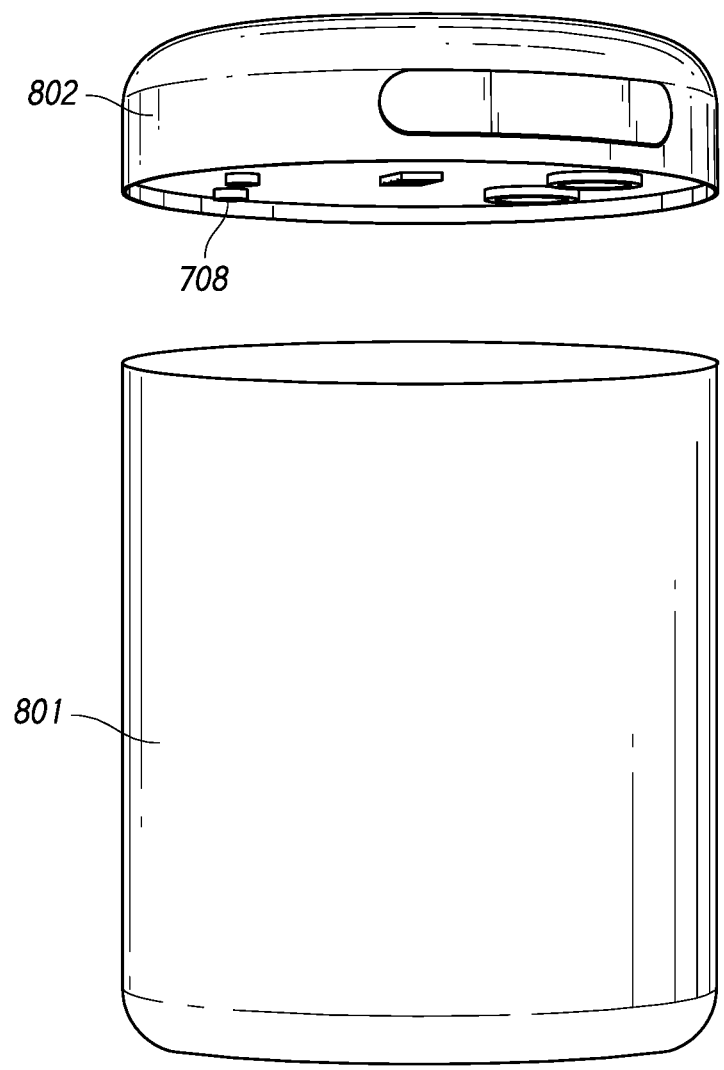
FIG. 12 is an isometric exploded view of a storage system in accordance with an embodiment of the technology.

FIG. 12 is an isometric exploded view of a storage system with container 801 and lid 802 with an analyzer, in accordance with an embodiment of the technology. The embodiment mentioned above may also be used in conjunction with a complementary bean storage container 801 with the features of the sensing base integrated into a sensing lid 802. In this embodiment, the sensing lid or bean storage container may contain a one-way vacuum pump valve 708 to connect to an internal or external vacuum pump mechanism to evacuate or displace the atmosphere from the bean storage container. Doing so removes the beans' exposure to oxygen and thereby prolongs their freshness.

In an alternate embodiment, the gas sensors, temperature sensor, and other electronic components are located in the removable lids of the grinder. This provides the advantage of placing the sensor very near the beans themselves, as opposed to sensing at a distance through the headspace connection tube. It also allows for alternate methods of sensing the beans' chemical composition, including infrared spectroscopy or solid phase micro extraction via a surface acoustic wave sensor system. The temperature sensing may also be accomplished through infrared temperature sensing. Such an embodiment can also include a connection between the electronic components of the removable lid and the sensor base microcontroller. In some embodiments, the container 801 can connect to a sensing base, which can analyze the contents of the container 801.

Figure 13:
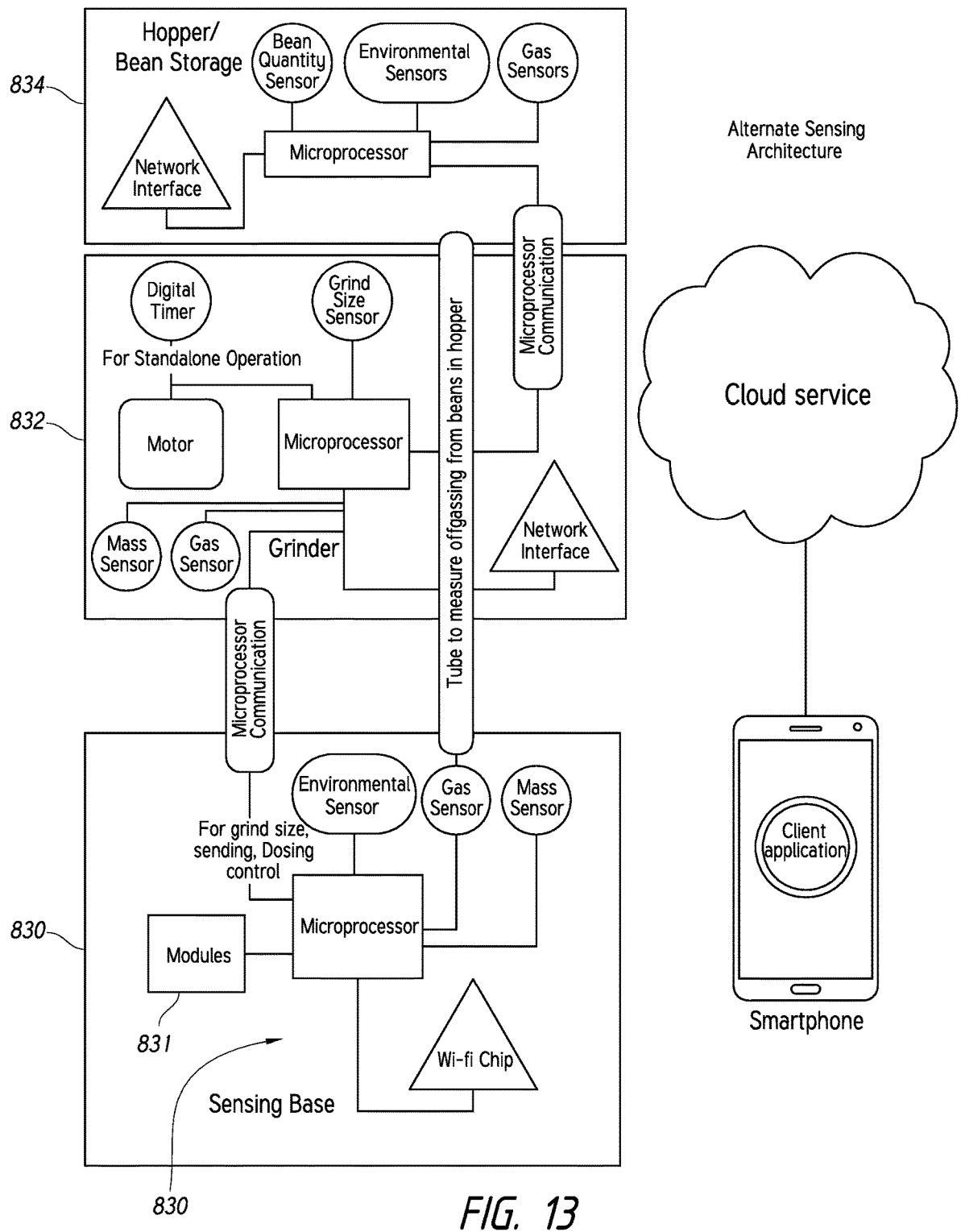
FIG. 13 is a diagram illustrating a grinding system and an environment in which the grinding system may operate.

FIG. 13 is a diagram illustrating an environment in which a grinding system may operate. The grinding system can have an alternative sensing architecture. The sensing functions, processing, and communication may take place in any or all of the sensing base 833, grinder 832, or hopper/bean storage area 834. A controller 830 can include memory with modules 831, including sensor calibration modules, compensation modules, estimation modules, or other suitable modules. Sensor calibration modules can be used to periodically calibrate the sensors based upon environmental conditions. The compensation modules can compensate for external factors that can affect sensor readings. For example, the compensation module can be configured to compensate for one or more environmental conditions that affect operation emission sensors. In VOC sensor embodiments, the compensation module can compensate for temperature affects in the operation of VOC sensors. A correction factor can be determined based on temperature readings or other detected environmental data from environment sensors. The environment sensors can be temperature sensors, humidity sensors, or light sensors.

The gas sensors, temperature sensor, and other electronic components are located in the removable lid of the grinder. This provides the advantage of placing the sensor very near the beans themselves, as opposed to sensing at a distance through the headspace connection tube. It also allows for alternate methods of sensing the beans' chemical composition, including infrared spectroscopy or Solid Phase Micro Extraction via a Surface Acoustic Wave sensor system. The temperature sensing may also be accomplished through infrared temperature sensing. An embodiment of this nature would also include a connection between the electronic components of the removable lid and the sensor base microcontroller.

In yet another alternate sensing architecture, the sensing functions, processing, and communication may take place in any or all of the sensing base, grinder, or hopper/bean storage area. Various components of grinding systems can include controllers, memory, and one or more processors. Controllers can include one or more processors with circuitry configured to execute instructions. In some embodiments, the controllers disclosed herein can be computing devices that control the operation of grinders based on, for example, desired amount of grounds, fineness of grounds, or the like. For example, a controller can include The components of systems disclosed herein can be interconnected by any form or medium of digital data communication (e.g., a communication network). For example, the grinding systems, analyzers, containers, and components can be in communication with another component, computing device (e.g., computer), and/or data service. Examples of communication networks include a local area network ("LAN") and a wide area network ("WAN"), an inter-network (e.g., the Internet), and peer-to-peer networks (e.g., ad hoc peer-to-peer networks).

Figure 14:
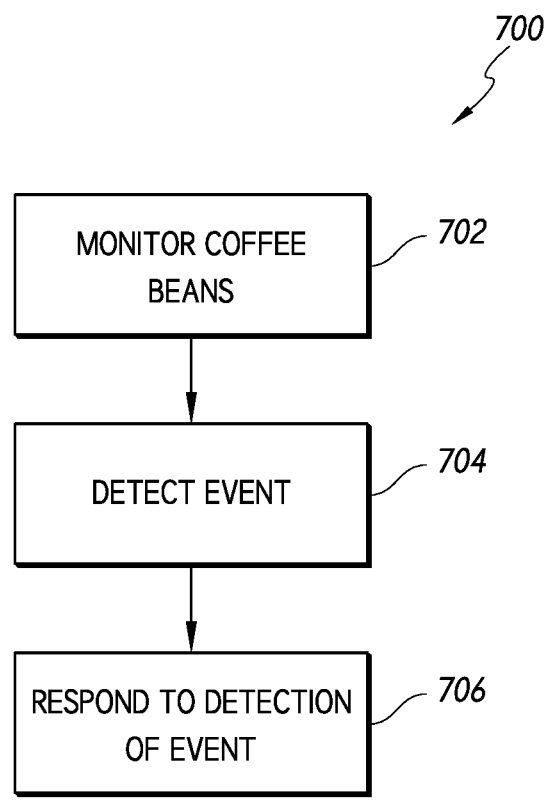
FIG. 14 is a flowchart of a method of operation in accordance with an embodiment of the technology.

FIG. 14 is a flowchart of a method 900 of operation in accordance with an embodiment of the technology. Generally, the coffee grinder can monitor coffee beans to identify events. The coffee grinder can respond to detection of an event by notifying the user, initiating action, or the like. Details of the method 900 are discussed in connection with coffee bean grinder systems and are discussed below.

At block 902, the grinder system can monitor coffee beans. Input from the user can be used to determine the frequency of monitoring and events of interest. A monitoring program can be selected based on the characteristics of the coffee beans and can use a freshness algorithm to determine freshness information. The freshness information can be analyzed to identify events, such as coffee beans becoming stale, as block 904. In other embodiments, the event at block 904 can be coffee beans reaching a minimum level so the user can refill the coffee grinder. In other embodiments, the event at block 904 can be based on the period of time the coffee beans are held within the grinder.

At block 906, the coffee grinder can respond to detection of the event. A user can select event triggers. An event notification can be sent to a user via instant messenger, email, visual or audible alert, or the like. In one embodiment, the coffee grinder sends an event notification to remote server, which then communicates with a user's remote device.

In use, a grinder system can acquire coffee bean data and can detect one or more events associated with the collected data and automatically send an alert for notifying the user based on the one or more events. The user can view the alert, data associated with detected events, and recommended actions, such as empty the grinder, refill grinder, or purchase coffee beans. The coffee grinders themselves can indicate an event. For example, a light indicator 603 in FIG. 9 can turn on when an event is detected. Additionally or alternatively, the coffee grinder 602 can include an event indicator 604 to provide viewing of information. This allows a user to track the characteristics of the beans and also to provide notification to user when the beans should be discarded. In other embodiments, the light indicator 603 can be turned on when the coffee grinder is almost empty. The light indicator 603 can be located on an input device 606. This can notify the user that the coffee grinder should be refilled with fresh beans. The sensing base 601 can also include event indicators, freshness level indicators, or the like. The coffee bean data can include, without limitation, freshness information, roasting information, environmental information (e.g., temperature data, chemical presence data, or commendations thereof), or the like. The position, number, and configuration of the indicators can be selected based on the number of characteristics being monitored, preferred notification means, and other desired functionality.

While particular aspects of the present subject matter described herein have been shown and described, it will be apparent to the reader that, based upon the teachings herein, changes and modifications can be made without departing from the subject matter described herein and its broader aspects, and, therefore, the appended claims are to encompass within their scope all such changes and modifications as are within the true spirit and scope of the subject matter described herein. Although some of the embodiments are described with respect to coffee beans, the embodiments can be suitable for other foodstuff. For example, the grinding system 90 of FIG. 1 can be used to store and grind spices, nuts, dried fruit/vegetables, or the like. The dosing 508 of FIG. 8 can be an amount of ground spice. In some embodiments, a recipe can be used to automatically determine the amount of ground spice to produce. The analyses, algorithms, behavior insights, and techniques can be used and modified to analyze, monitor, evaluate a wide range of items. The number, detection capabilities, and sensitivity of the sensors can be selected based on the characteristics of the items, including typical emissions or changes associated with freshness, deterioration, staling, etc. While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A system, comprising:
a holding chamber configured to hold unground coffee beans;
a sensing apparatus including at least one emission sensor and being configured to detect one or more emissions from the unground coffee beans held in the holding chamber, wherein the one or more emissions from the unground coffee beans include one or more volatile organic compounds (VOC) gases and/or one or more gases indicative of unground coffee bean deterioration; and
a controller communicatively coupled to the sensing apparatus and programmed to determine freshness information about the unground coffee beans based on output from the at least one emission sensor, and
one or more environmental parameters associated with the unground coffee beans,
wherein the controller is programmed to determine a freshness value (F) for the coffee beans as follows:

$$F = \frac{S \times \alpha_T \times \lambda_Q \times \alpha_B \times \alpha_R \times \alpha_A}{\text{Ideal } Freshness_{specific\ bean}}$$

where
S is a sensor reading from the at least one emission sensor,
$\alpha_T$ is a temperature correction factor at a particular temperature,
$\lambda_Q$ is a bean quantity correction factor,
$\alpha_B$ is a bean correction factor,
$\alpha_R$ is a roast date correction factor,
$\alpha_A$ is a bean age for the coffee beans, and
Ideal Freshness$_{specific\ bean}$ is a freshness value for the coffee beans.

2. The system of claim 1, wherein the controller includes
a bean analysis module configured to determine the freshness information for the coffee beans based on output from the at least one emission sensor, wherein the freshness information includes the freshness value; and
a compensation module configured to compensate for one or more environmental conditions that affect detection of the one or more emissions by the at least one emission sensor and/or temperature-induced emissions from the coffee beans.

3. The system of claim 2, wherein the compensation module is configured to compensate for temperature effects of the at least one emission sensor.

4. The system of claim 1, wherein the controller is configured to receive and store the Ideal Freshness$_{specific\ bean}$.

5. The system of claim 1, wherein the controller is programmed to receive user input indicating a user-defined event and to perform an action in response to the user-defined event identified based on the one or more emissions.

6. The system of claim 5, wherein performing the action includes alerting a user, setting grind fineness settings, and/or shutting off power to a motor that drives the grinding element.

7. The system of claim 1, wherein the controller includes:
a processor; and
memory containing instructions that when executed by the processor cause the controller to compensate for at least one environmental condition that affects detection of the one or more emissions by the at least one emission sensor.

8. The system of claim 1, wherein the controller includes a program for compensating for temperature effects on the at least one emission sensor.

9. The system of claim 1, wherein the controller is programmed to
store at least event trigger,
detect one or more events based on the stored at least event trigger and the signals from the at least one emission sensor, and
automatically initiating a user notification based on the detected one or more events.

10. The system of claim 1, further comprising one or more user input elements operable to set event triggers, and wherein the one or more user input elements include at least one touchscreen, button, keypad, or dial.

11. The system of claim 1, wherein the environmental parameters include humidity information, light information, and/or temperature information.

12. The system of claim 1, wherein the controller is programmed to determine when the unground coffee beans are stale based on the freshness information.

13. The system of claim 1, wherein
the sensing apparatus analyzes gases to determining a concentration of the one or more emissions from the unground coffee beans, and
the controller is programmed to determine the freshness value of the unground coffee beans using the determined concentration of the one or more emissions.

14. A system, comprising:
a portable electric coffee grinder including a holding chamber and a grinding element, wherein the holding chamber is configured to hold unground coffee beans; and
a sensing base configured to support the portable electric coffee grinder and including a sensing apparatus, wherein the sensing base is detachably coupleable to the portable electric coffee grinder so as to establish fluid communication with the holding chamber, wherein the sensing apparatus includes at least one emission sensor and is configured to detect one or more emissions from the unground coffee beans held in the holding chamber, wherein the one or more emissions from the unground coffee beans include one or more volatile organic compounds (VOC) gases and/or one or more gases indicative of unground coffee bean deterioration; and
a controller communicatively coupled to the sensing apparatus and programmed to determine freshness information about the unground coffee beans based on output from the at least one emission sensor, and
one or more environmental parameters associated with the unground coffee beans.

15. The system of claim 1, wherein the controller is further programmed to
receive a detected value from the at least one emission sensor,
compare the detected value to a set threshold value, and
cause a notification to be sent to a user in response to the detected value being above the set threshold value.

* * * * *